(12) United States Patent
Brooks et al.

(10) Patent No.: US 11,957,807 B2
(45) Date of Patent: Apr. 16, 2024

(54) CLEANING ROBOT

(71) Applicant: Robust AI, Inc., San Carlos, CA (US)

(72) Inventors: Rodney Allen Brooks, San Francisco, CA (US); Dylan Bourgeois, San Francisco, CA (US); Crystal Chao, San Francisco, CA (US); Alexander Jay Bruen Trevor, San Francisco, CA (US); Mohamed Rabie Amer, San Francisco, CA (US); Anthony Sean Jules, Hillsborough, CA (US); Gary Fred Marcus, Vancouver (CA)

(73) Assignee: Robust AI, Inc., San Carlos, CA (US)

( * ) Notice: Subject to any disclaimer, the term of this patent is extended or adjusted under 35 U.S.C. 154(b) by 519 days.

(21) Appl. No.: 17/208,672

(22) Filed: Mar. 22, 2021

(65) Prior Publication Data

US 2021/0346543 A1 Nov. 11, 2021

Related U.S. Application Data

(60) Provisional application No. 63/022,349, filed on May 8, 2020, provisional application No. 63/022,348, filed on May 8, 2020.

(51) Int. Cl.
*A61L 2/24* (2006.01)
*A47L 11/40* (2006.01)
(Continued)

(52) U.S. Cl.
CPC ............. *A61L 2/24* (2013.01); *A47L 11/4011* (2013.01); *A47L 11/405* (2013.01); *A61L 2/10* (2013.01); *B25J 9/1664* (2013.01); *B25J 9/1674* (2013.01); *B25J 11/0085* (2013.01); *B25J 15/0014* (2013.01); *B25J 18/00* (2013.01); *G01C 21/206* (2013.01); *G02B 3/08* (2013.01); *G02B 5/208* (2013.01); *G02B 5/26* (2013.01); *G02B 26/0875* (2013.01); *G05D 1/0094* (2013.01); *G05D 1/0214* (2013.01); *G05D 1/0246* (2013.01);
(Continued)

(58) Field of Classification Search
CPC .................................... A61L 2/10; A61L 2/24
See application file for complete search history.

(56) References Cited

U.S. PATENT DOCUMENTS

| 4,028,135 A | 6/1977 | Vig et al. |
|---|---|---|
| 6,865,446 B2 | 3/2005 | Yokono et al. |

(Continued)

FOREIGN PATENT DOCUMENTS

WO 2018233858 A1 12/2018

OTHER PUBLICATIONS

Int'l Application Serial No. PCT/US21/24416, Int'l Search Report and Written Opinion dated Jun. 10, 2021.

*Primary Examiner* — Donald R Spamer
*Assistant Examiner* — Priscilla Browning
(74) *Attorney, Agent, or Firm* — Polygon IP, LLP

(57) ABSTRACT

A cleaning robot may determine a three-dimensional model of a physical environment based on data collected from one or more sensors. The cleaning robot may then identify a surface within the physical environment to clean. Having identified that surface, the robot may autonomously navigate to a location proximate to the surface, position an ultraviolet light source in proximity to the surface, and activate the ultraviolet light source for a period of time.

13 Claims, 24 Drawing Sheets

(51) Int. Cl.

| | | |
|---|---|---|
| *A61L 2/10* | (2006.01) | |
| *B25J 9/16* | (2006.01) | |
| *B25J 11/00* | (2006.01) | |
| *B25J 15/00* | (2006.01) | |
| *B25J 18/00* | (2006.01) | |
| *G01C 21/20* | (2006.01) | |
| *G02B 3/08* | (2006.01) | |
| *G02B 5/20* | (2006.01) | |
| *G02B 5/26* | (2006.01) | |
| *G02B 26/08* | (2006.01) | |
| *G05D 1/00* | (2006.01) | |

(52) U.S. Cl.
CPC ........ *A47L 2201/04* (2013.01); *A61L 2202/11* (2013.01); *A61L 2202/14* (2013.01); *A61L 2202/16* (2013.01); *A61L 2202/17* (2013.01); *A61L 2202/25* (2013.01); *G05B 2219/50391* (2013.01)

(56) References Cited

U.S. PATENT DOCUMENTS

| | | |
|---|---|---|
| 6,925,679 B2 | 8/2005 | Wallach et al. |
| 8,428,781 B2 | 4/2013 | Chang et al. |
| 8,909,370 B2 | 12/2014 | Stiehl et al. |
| 9,757,486 B2 | 9/2017 | Dobrinsky et al. |
| 10,279,476 B2 | 5/2019 | Jaekel et al. |
| 10,793,291 B2 | 10/2020 | Brown et al. |
| 2008/0106374 A1* | 5/2008 | Sharbaugh ............ G16Z 99/00 705/2 |
| 2010/0234993 A1* | 9/2010 | Seelinger ............ G05D 1/0251 700/254 |
| 2012/0305787 A1* | 12/2012 | Henson ................ A61L 2/10 250/492.1 |
| 2015/0088310 A1* | 3/2015 | Pinter ................ G16H 40/67 901/1 |
| 2016/0271803 A1 | 9/2016 | Stewart |
| 2016/0317690 A1* | 11/2016 | Dayton ................ A61L 2/00 |
| 2016/0354931 A1 | 12/2016 | Jones et al. |
| 2017/0049915 A1* | 2/2017 | Brais ................ H05B 47/115 |
| 2017/0080117 A1* | 3/2017 | Gordon ................ A61L 2/084 |
| 2017/0246331 A1 | 8/2017 | Lloyd |
| 2018/0104368 A1 | 4/2018 | Dobrinsky et al. |
| 2018/0116479 A1 | 5/2018 | Gilbert, Jr. et al. |
| 2019/0219409 A1 | 7/2019 | Tan et al. |
| 2019/0224853 A1 | 7/2019 | Gewecke et al. |
| 2020/0086487 A1 | 3/2020 | Johnson et al. |
| 2020/0094418 A1 | 3/2020 | Mika et al. |
| 2021/0053207 A1 | 2/2021 | Romanov et al. |

\* cited by examiner

The energy twice as far from the source is spread over four times the area, hence one-fourth the intensity

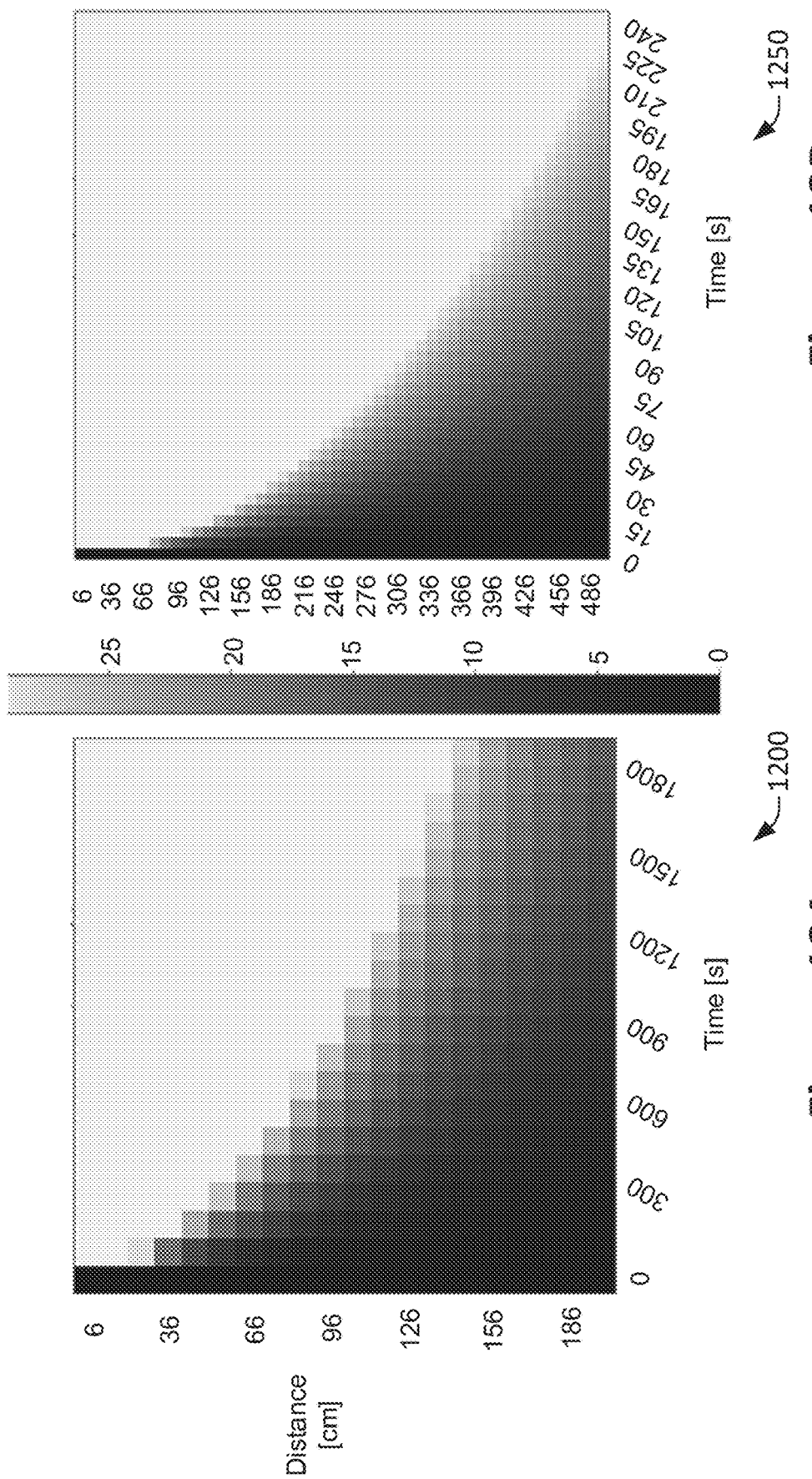

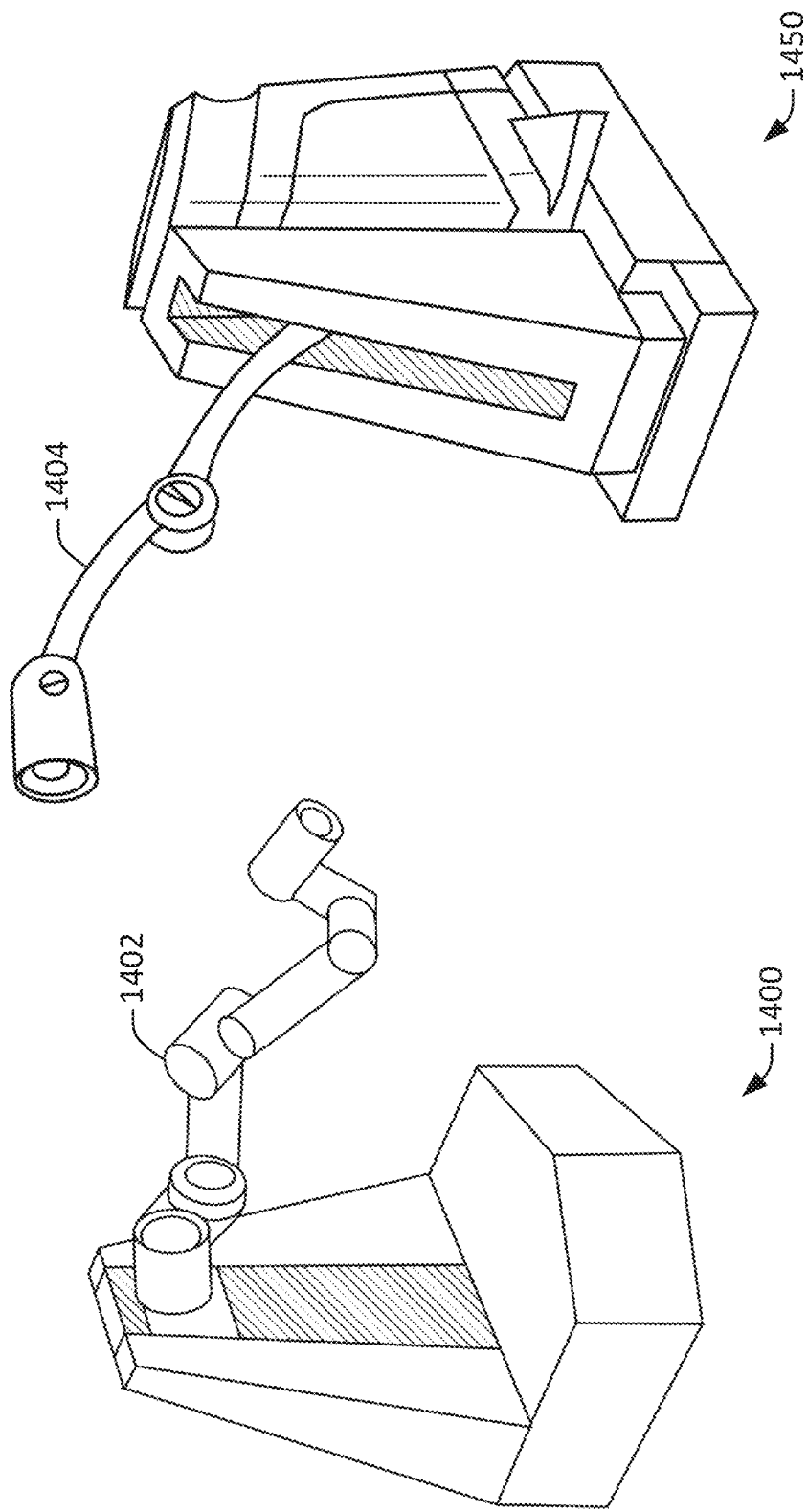

CLEANING ROBOT

CROSS-REFERENCE TO RELATED APPLICATION

The present application claims priority under 35 U.S.C. 120 to U.S. Provisional Application No. 63/022,348 by Brooks et al., titled "A CLEANING ROBOT", filed May 8, 2020, and to U.S. Provisional Application No. 63/022,349 by Brooks et al., titled "ROBOTIC SOCIAL INTERACTION", filed May 8, 2020, both of which are hereby incorporated by reference in their entirety and for all purposes.

COPYRIGHT NOTICE

A portion of the disclosure of this patent document contains material which is subject to copyright protection. The copyright owner has no objection to the facsimile reproduction by anyone of the patent document or the patent disclosure as it appears in the United States Patent and Trademark Office patent file or records but otherwise reserves all copyright rights whatsoever.

TECHNICAL FIELD

The present disclosure relates generally to robotics, and more specifically to robotic cleaning solutions.

DESCRIPTION OF RELATED ART

Conventional approaches to cleaning often involve manual activity by humans, but such approaches have numerous drawbacks. For example, humans can clean surfaces using chemical means. However, manual cleaning with chemicals can expose humans to potentially dangerous chemicals and pathogens. Further, manual cleaning with chemicals often results in incomplete cleaning that falls far short of standards for sterilization or even disinfection. As another example, humans can clean surfaces by activating a handheld UV light source. However, such an approach risks exposing humans to excessive UV energy, risks incomplete cleaning, and requires significant manual activity.

Other conventional approaches to cleaning involve automated, powerful UV light sources. However, such an approach often involves moving a powerful light source into an area and then evacuating the area while the cleaning is completed. Such approaches are typically restricted to optically-sealed rooms or shelters from which all people and animals must leave while cleaning occurs. The risk to humans is significant since a safe dosage would be exceeded at one meter distance in a matter of seconds. In addition, such approaches require massive energy consumption. Such powerful UV light sources also can degrade plastics, equipment, and other materials present in the room. Some powerful UV lamps emit ozone, a greenhouse gas. Some powerful UV lamps also contain mercury (Hg), which both creates sanitary risks and imposes an environmental cost.

OVERVIEW

According to various embodiments, techniques and mechanisms described herein provide for systems, devices, methods, and machine readable media for robotic cleaning solutions. A robot may include a sensor module operable to collect sensor data characterizing a physical environment around the robot. A processor at the robot may determine a three-dimensional model of the physical environment based at least in part on the sensor data. The processor may also identify a designated surface to clean within the physical environment based at least in part on the three-dimensional model. A mobility apparatus at the robot may be operable to navigate the physical environment. The processor may be operable to cause the robot to autonomously navigate to a designated location proximate to the designated surface via the mobility apparatus. An ultraviolet light source at the robot may be operable to emit electromagnetic radiation in a range capable of cleaning the designated surface. The processor may be further operable to clean the designated surface by autonomously activating the ultraviolet light source for a designated period of time.

According to various embodiments, the robot may include a robotic arm capable of movement with respect to the robot in one or more dimensions. The ultraviolet light source may be coupled with the robotic arm. The processor may be further operable to autonomously move the robotic arm to bring the ultraviolet light source in proximity with the designated surface. The ultraviolet light source may be capable of orientation with respect to the robotic arm in one or more dimensions. The processor may be further operable to determine a path through space for the robotic arm that will expose the designated surface to a level of electromagnetic radiation that exceeds a designated threshold. Autonomously moving the robotic arm may involve moving the robotic arm along the path through space.

In some implementations, the processor may be further operable to identify a presence and a corresponding location of a human being within the physical environment. Autonomously navigating to the designated location may involve avoiding the corresponding location. The processor may be further operable to predict a level of UV exposure to the human from activating the ultraviolet light source, to activate the ultraviolet light source only when the predicted level of UV exposure does not exceed a designated threshold, to predict a level of UV exposure to the human from activating the ultraviolet light source, and/or to deactivate the ultraviolet light source when the predicted level of UV exposure exceeds a designated threshold. The robot may include a user interface operable facilitating communication between the robot and a human located proximate to the robot in the physical environment.

In some embodiments, the robot may be operable to autonomously determine that a human is moving along a path that is predicted to approach the robot, autonomously deactivate the ultraviolet light source, and autonomously navigate away from the predicted path. Alternatively, or additionally, the robot may be operable to autonomously determine that the human has moved away from the designated surface and autonomously resume cleaning the designated surface.

In some implementations, the designated surface may be one of a plurality of surfaces within the physical environment. The processor may be further configured to identify a subset of the surfaces for cleaning, to autonomously determine a plan for cleaning each of the subset of the surfaces, and/or to autonomously operate the mobility apparatus and the ultraviolet light source to implement the plan. The sensor module may include a camera, and the sensor data may include image data collected from the physical environment. The sensor module may include a depth sensor, and the sensor data may include depth information indicating a plurality of distances from the depth sensor to a plurality of objects within the physical environment. The robot may include a communication interface operable to receive an instruction from a remote communication device that designates a portion of the physical environment for cleaning.

BRIEF DESCRIPTION OF THE DRAWINGS

The included drawings are for illustrative purposes and serve only to provide examples of possible structures and operations for the disclosed inventive systems, apparatus, methods and computer program products for robotic cleaning solutions. These drawings in no way limit any changes in form and detail that may be made by one skilled in the art without departing from the spirit and scope of the disclosed implementations.

FIG. 11A, FIG. 11B, FIG. 12A, and FIG. 12B illustrate plots generated in accordance with one or more embodiments.

FIG. 14A, FIG. 14B, FIG. 15A, FIG. 15B, FIG. 15C, FIG. 16, FIG. 17, FIG. 18, FIG. 19, FIG. 20, and FIG. 21 illustrate cleaning robots, configured in accordance with one or more embodiments.

DETAILED DESCRIPTION

Figure 1:
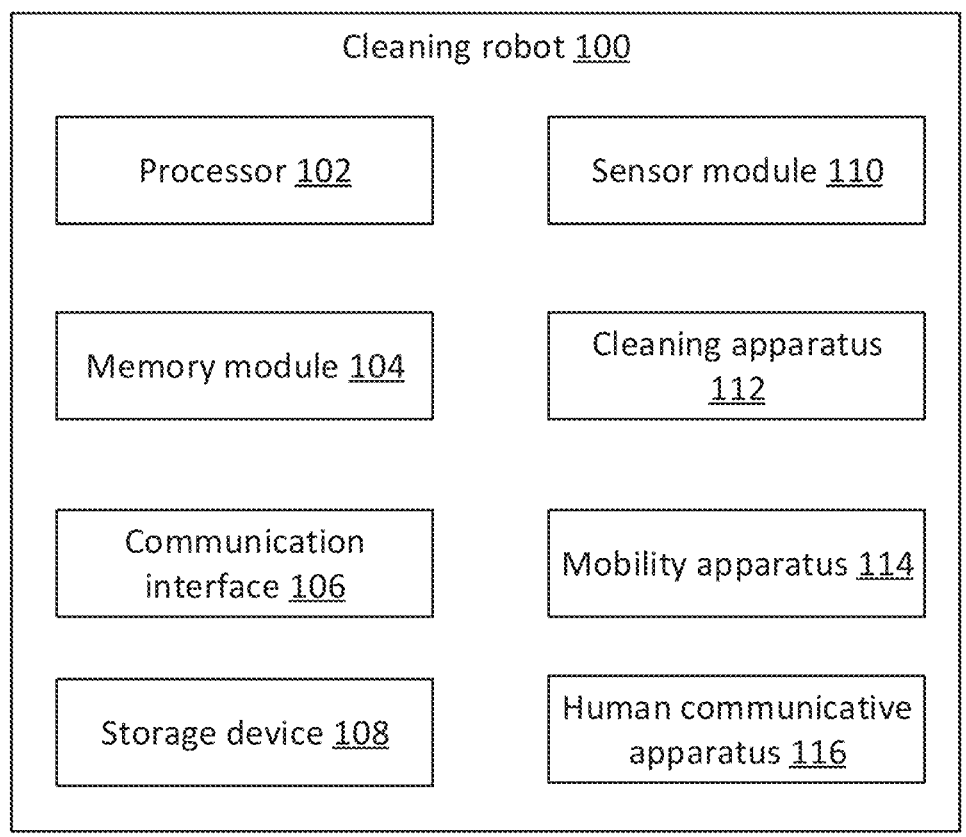
FIG. 1 illustrates an architecture diagram for a cleaning robot, configured in accordance with one or more embodiments.

Techniques and mechanisms described herein are directed to a robotic cleaning solution. A robot may navigate an area for the purpose of cleaning some or all of the area. The area may be otherwise occupied by people who are present for purposes associated with the location. Accordingly, the robot may engage in social accommodation, in which it attempts to accomplish its cleaning task while taking into account the presence, goals, and trajectories of the people.

According to various embodiments, the robot may be equipped with one or more cleaning tools, such as one or more ultraviolet (UV) power sources. The term "UV light" generally refers to electromagnetic radiation in the 10 nm-400 nm wavelength range. Cleaning applications of UV radiation, sometimes referred to as Ultra-Violet Germicidal Irradiation (UVGI), can apply illumination in the UVC range of wavelengths, between approximately 100 nm-280 nm, corresponding to the range of maximum response by most targeted pathogens.

Depending on the configuration, a cleaning tool such as a UV power source may be oriented in two, three, four, five, six, or any number of suitable dimensions, independent of the movement of the robot itself. In the case of a UV power source, the robot may position the UV power source close to a cleaning target and then activate the UV power source. The robot may then move the UV power source through a trajectory, either by moving the power source, moving the robot, or some combination thereon.

According to various embodiments, the robot may be equipped to accommodate the presence of people within the area of cleaning. For example, the robot may monitor people nearby and estimate levels of UV radiation the people may be receiving. If the robot determines that radiation may bring the total dose to any human above a safety threshold, then the robot may avoid activating the UV power source or may deactivate the UV power source if it has already been activated. As another example, the robot may provide social cues to people as to the robot's actions. For instance, the robot may indicate what it is doing and/or how long the cleaning action will continue. As yet another example, the robot may interrupt a cleaning process and/or move to a different location when it determines that it should defer to the activity of humans, animals, or other robots.

In some implementations, the robot may be guided in its cleaning activity based on communication with a remote computing device such as a control computer having access to a database system. Alternatively, or additionally, the robot may report its actions to such a system.

In some implementations, the robot may coordinate with other robots. The other robots may be configured to perform complementary cleaning activities or may be focused on other tasks. Each robot may be directed by a central command and control apparatus. Alternatively, or additionally, the robots may communicate with each other directly.

In some implementations, the robot may communicate with nearby people. For example, the robot may receive cleaning instructions from a nearby person. As another example, the robot may receive instructions about social accommodation from a nearby person. The robot may be configured to verify the authority of the person to issue such instructions. For instance, the robot may be configured to ascertain the person's identity and/or role through any of various authentication mechanisms.

In some embodiments, the term "cleaning" may encompass any or all of a variety of concepts. At the lowest level, "sanitation" refers to reducing the density amount of pathogenic microbes on a surface. The term "disinfection" refers to a strong sanitization in which specific pathogens are almost totally removed. "Decontamination" refers to the removal of specific dangerous pathogens. At the highest level, "sterilization" refers to the removal of all pathogens from a surface. The term "power" refers to energy over time and may be measured in Watts (i.e., Joules/second). The term "intensity" refers to the amount of power distributed on a surface and may be measured in Watts per area of surface. The term "dose" refers to intensity received over time and may be measured in Joules per area of surface, or equivalently Watts multiplied by time and divided by surface area.

In contrast to conventional approaches, techniques and mechanisms described herein provide for the safe, effective, comprehensive, and automated cleaning. For example, techniques and mechanisms described herein may facilitate the automated cleaning of a hospital, laboratory, restaurant, retail establishment, industrial facility, schools, or other environments.

In some implementations, one or more cleaning robots may navigate a physical environment to clean surfaces and objects within the environment. For example, each cleaning robot may be equipped with one or more relatively low power, directional UV light sources that the robot brings into close proximity with a surface to be cleaned. Because the UV light source is relatively lower powered and/or directional, human exposure can be limited or prevented. For instance, the robot can monitor the environment to avoid both inconveniencing humans and exposing humans to excessive UV energy. The robot can then automatically navigate to a charging or docking station when its tasks have been completed.

In particular embodiments, techniques and mechanisms described herein may facilitate the cleaning of an environment such as a hospital. The complexity, number of pathogens, and high occupancy of hospital environments makes the cleaning of such environments both extremely important and yet difficult via conventional means. However, using techniques and mechanisms described herein, one or more robots may continuously or periodically traverse a hospital environment to clean objects and surfaces. In particular, a robot using a targeted, low-powered UV light source may unobtrusively and safely navigate the environment to opportunistically clean surfaces and objects when such cleaning can be performed without inconveniencing humans or exposing humans to excessive UV radiation.

In particular embodiments, a cleaning robot can also perform tasks in a socially aware way, for instance by recognizing individuals based on their roles as doctors, nurses, patients, administrators, maintenance workers, and/or members of the public, and then treating individuals differently based on those roles. For example, the cleaning robot may place a very high priority on avoiding doctors and nurses, who may be in a hurry to provide medical services. As another example, the cleaning robot may be configured to respond to instructions from maintenance workers and administrators. However, the cleaning robot may be less accommodating of other individuals, such as members of the general public.

FIG. 1 illustrates an architecture diagram for a cleaning robot 100, configured in accordance with one or more embodiments. According to various embodiments, the cleaning robot 100 may be configured in a variety of form factors so long as it includes the ability to relocate and clean a surface. The cleaning robot 100 includes a processor 102, a memory module 104, a communication interface 106, a storage device 108, a sensor module 110, a cleaning apparatus 112, a mobility apparatus 114, and a human communicative apparatus 116.

According to various embodiments, the cleaning robot 100 may include one or more processors 102 configured to perform operations described herein. The memory module 104 may include one or more transitory memory elements, such as random access memory (RAM) modules. The storage device 108 may be configured to store information such as computer programming language instructions and/or configuration data.

In some implementations, the cleaning robot 100 may include one or more communication interfaces 106 configured to perform wired and/or wireless communication. For example, the communication interface 106 may include a WiFi communication module. As another example, the communication interface 106 may include a wired port such as a universal serial bus (USB) port, which may be connected when the cleaning robot couples with a docking or charging port or device.

According to various embodiments, the sensor module 110 may include one or more of various types of sensors. Such sensors may include, but are not limited to: visual light cameras, infrared cameras, microphones, Lidar devices, Radar devices, chemical detection devices, near field communication devices, and accelerometers.

In particular embodiments, the sensor module 110 may communicate with one or more remote sensors. For example, an environment may be equipped with one or more of various types of sensors, data from which may be relayed to cleaning robots within the vicinity.

According to various embodiments, the cleaning apparatus 112 may include one or more of a variety of suitable cleaning devices. Such devices may be chemical and/or radiation based. For instance, a cleaning device may be configured to emit UV radiation. Various types of UV light sources may be used. For example, a "point" LED may emit UV light, potentially with an angular range of emission. As another example, a cylindrical UV light may emit UV radiation in a relatively constant pattern along the axis of the cylinder and may potentially cover an angular range. Such sources may be combined in a fixed or variable pattern, for instance to provide a more powerful light source and/or to shape the UV emission pattern.

In particular embodiments, shielding may help to stop UV light from emitting in certain directions. Alternatively, or additionally, one or more reflectors or lenses may be used to help guide or focus UV light toward a target.

According to various embodiments, a cleaning device may be attached to the cleaning robot 100 in any of various ways. For example, the cleaning device may be attached in a fixed orientation relative to a robot drive mechanism. As another example, the cleaning device may be attached to the cleaning robot via a robotic arm having any of a variety of possible geometries.

In particular embodiments, a UV light may be fixed in a downward pointing on a robotic arm having three degrees of freedom of spatial mobility, allowing the arm to be positioned at different points of space along three axes. In such a configuration, the cleaning device could be positioned to clean a table top by positioning the UV light at a designated distance from the table top through a combination of movement of the robotic arm and the robot itself. The cleaning device could be positioned in a fixed location over the table top, or could clean the table top from different locations. For example, larger table tops may require cleaning from more locations.

In particular embodiments, a UV light may be configured with four, five, six, or more degrees of freedom. For example, a robotic arm may have three degrees of freedom. Then, a UV light positioned on the arm may itself be configured for movement in three dimensions. In this case, the movement of the robotic arm and the UV light may be combined to trace a potentially complex trajectory through space in order to irradiate a target from multiple directions. For instance, a cleaning device may be configured with 5 degrees of freedom in order to irradiate a spherical door handle from the left, from the right, from above, and from below without requiring the robot itself to move.

According to various embodiments, the mobility apparatus may include one or more of any suitable mobility devices. Such devices may include, but are not limited to, one or more motorized wheels, balls, treads, or legs. In some configurations, the mobility apparatus may include one or more rotational and/or gyroscopic elements configured to aid in mobility and/or stability.

According to various embodiments, the robot may communicate directly with a human via the human communicative apparatus 116. The human communicative apparatus 116 may include one or more components for conducting visible and/or audible communication with a human. For instance, the human communicative apparatus 116 may include one or more display screens, LEDs, motors, robotic arms, motion sensors, speakers, microphones, or other such components. For example, the human communicative apparatus 116 may include a display screen coupled with a motor that may be used to provide visual cues about the robot's activities.

In particular embodiments, the cleaning robot 100 may be configured to communicate directly or indirectly with other robots in order to accomplish its tasks. For example, robots may share information to build up an accurate model of an environment, identify the location and/or trajectory of humans, animals, or objects, perform social accommodation. As another example, robots may coordinate to execute a cleaning plan. For instance, one cleaning robot may be interrupted in a task due to social accommodation. The cleaning robot may then move on to another cleaning task, while a different cleaning robot may then later perform the interrupted cleaning task. As yet another example, robots may coordinate to perform a single task. For example, one or two robots may position themselves so as to provide social cues such as warning lights or sounds, while another robot engages in high-intensity UV cleaning in a designated area.

Figure 2:
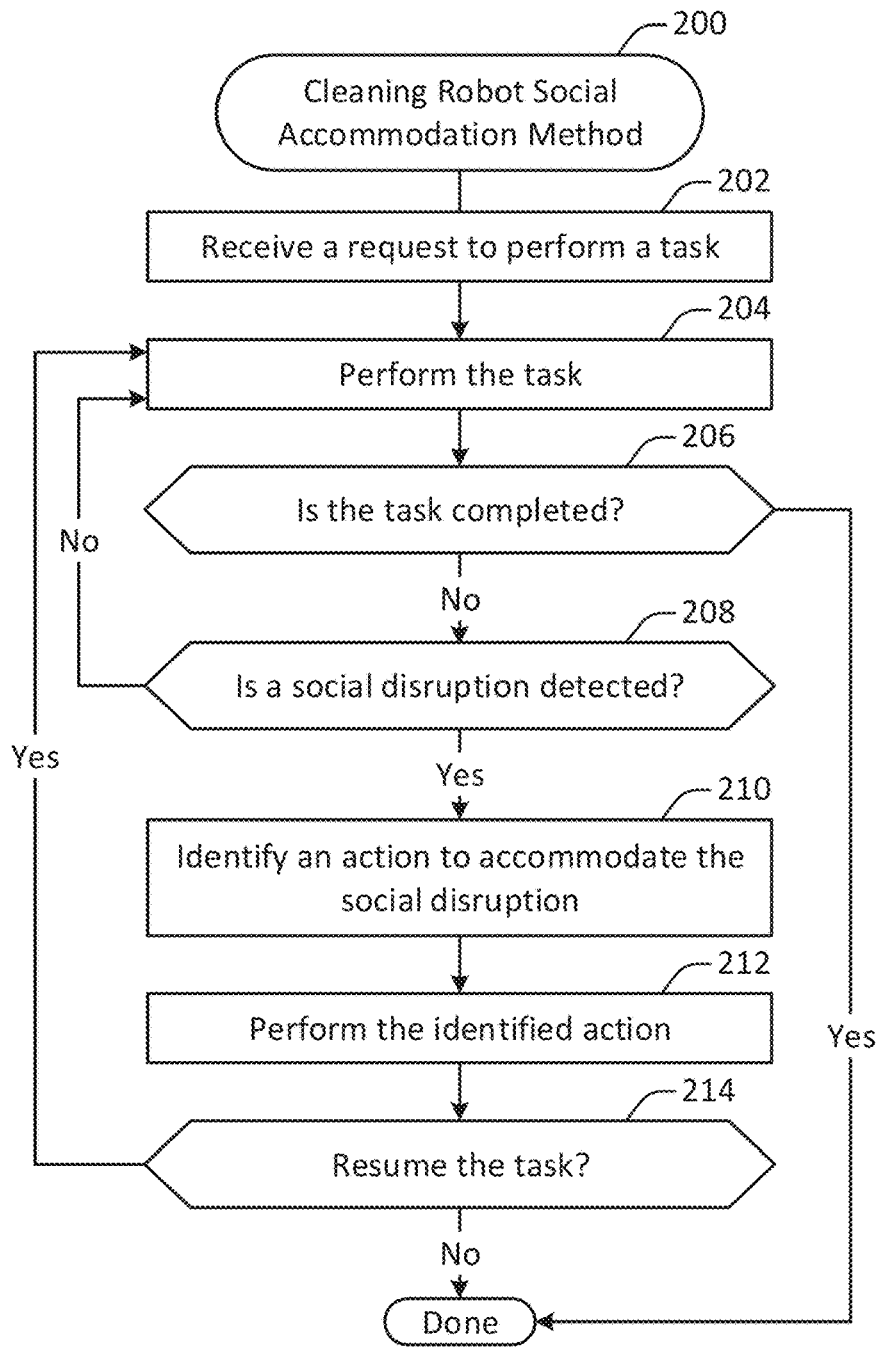
FIG. 2 illustrates a method for social accommodation by a cleaning robot, performed in accordance with one or more embodiments.

FIG. 2 illustrates a method 200 for social accommodation by a cleaning robot, performed in accordance with one or more embodiments. The method 200 may be performed by the cleaning robot as part of, or in addition to, the execution of any other operations.

A request to perform a task is received at 202. According to various embodiments, the task may include any operation capable of being performed by the cleaning robot. For example, the task may include cleaning an object or surface as discussed with respect to the method 300 shown in FIG. 3, waiting at a designated location, or any of the actions discussed with respect to operation 210 as being performed to accommodate a social disruption.

The task is performed at 204. A determination is made at 206 as to whether the task is completed. If the task is completed, then the method is finished. If the task is not completed, then a determination is made at 208 as to whether a social disruption is detected. An action to accommodate the social disruption is identified at 210, and the action is performed at 212. A determination is made at 214 as to whether to resume the task. Depending on the outcome of that determination, the task is resumed at 204 or the method is terminated. When the method is terminated, the cleaning robot may move on to the next task.

According to various embodiments, the detection of a response to social disruption may be pre-configured and/or dynamically determined based on a variety of characteristics such as the environment in which the cleaning robot is operating, the identity or role of a human associated with the social disruption, the urgency of the cleaning robot's tasks, instructions received from a human, and/or one or more safety considerations. Although a variety of specific examples are discussed herein, various configurations are possible.

In some implementations, a cleaning robot may be interrupted while cleaning a door handle by a person walking up behind the robot. In such a situation, the cleaning robot may predict that the human is likely to proceed through the door. Accordingly, the cleaning robot may stop cleaning and move out of the way. If the human proceeds through the door, then the cleaning robot may restart the cleaning process from the beginning because the human may have touched the door handle. If the human walks away without proceeding through the door, then the cleaning robot may resume the cleaning process without starting from the beginning.

In some implementations, a cleaning robot may be interrupted while cleaning a door handle by the door handle turning or the door opening from the other side. In such a situation, the cleaning robot may predict that a human is likely to use the door, even if no human has been specifically detected. Accordingly, the cleaning robot may stop cleaning and move out of the way, and resume cleaning once the door has been closed and no people are detected in close proximity. While waiting, the cleaning robot may monitor the door handle to determine if it is touched.

In some implementations, a cleaning robot may be interrupted while cleaning a table by people who sit at the table. In such a situation, the cleaning robot may cease cleaning the table and move on to the next task.

In some implementations, a cleaning robot may be interrupted while cleaning a faucet at a sink by a person who moves near the cleaning robot. In such a situation, the cleaning robot may cease cleaning and move out of the way. The cleaning robot may then observe whether the person touches any objects or surfaces such as a sink or faucet. When the person is gone, the cleaning robot may resume its task. If the person touched a surface or object, the cleaning robot may restart the cleaning process for that surface or object.

In some implementations, when a task is interrupted, the cleaning robot may wait either passively or actively. If passively waiting to resume a task, the cleaning robot may select a spot off to the side from the predicted paths along which people are most likely to walk. If actively waiting to resume a task, the cleaning robot may select another task to perform. For example, if interrupted while cleaning a door knob, the cleaning robot may clean a different surface while it waits to resume cleaning the door knob. As another example, if interrupted while cleaning a faucet at a sink, the cleaning robot may move to a different faucet at a different sink.

In some implementations, a social disruption may constitute the actual movement of a human into close proximity with the cleaning robot. Alternatively, or additionally, a social disruption may constitute the predicted movement of a human into close proximity with the cleaning robot. For instance, a robot engaged in a cleaning task may sense its environment and predict that a human is moving along a path that will bring the human in close proximity to the cleaning robot. If so, the robot may treat the human's movement as a social disruption even though the human is not yet actually located proximate to the cleaning robot.

In some implementations, a cleaning robot may determine whether or not to wait and resume a task or move on to another task based on, for instance, predicted human activity. For example, the cleaning robot may predict that a human is likely to enter and quickly leave an area based on the human's movement along a path. In such a situation, the cleaning robot may elect to wait for the human to pass and then resume the task. As another example, the cleaning robot may predict that a social disruption is likely to be longlasting, such as when a human sits down at a table. In such a situation, the cleaning robot may elect to move on to a different task.

According to various embodiments, the cleaning robot may strategically determine whether to employ active or passive waiting based on factors such as whether the area is crowded with people, the time required to switch between tasks, the time scheduled in which to complete one or more tasks, and/or instructions from humans.

In particular embodiments, the method 200 may include one or more operations not shown in FIG. 2. For example, the cleaning robot may log or report a social disruption, an action performed in response to the social disruption, and/or the robot's success or failure at performing the requested task.

Figure 3:
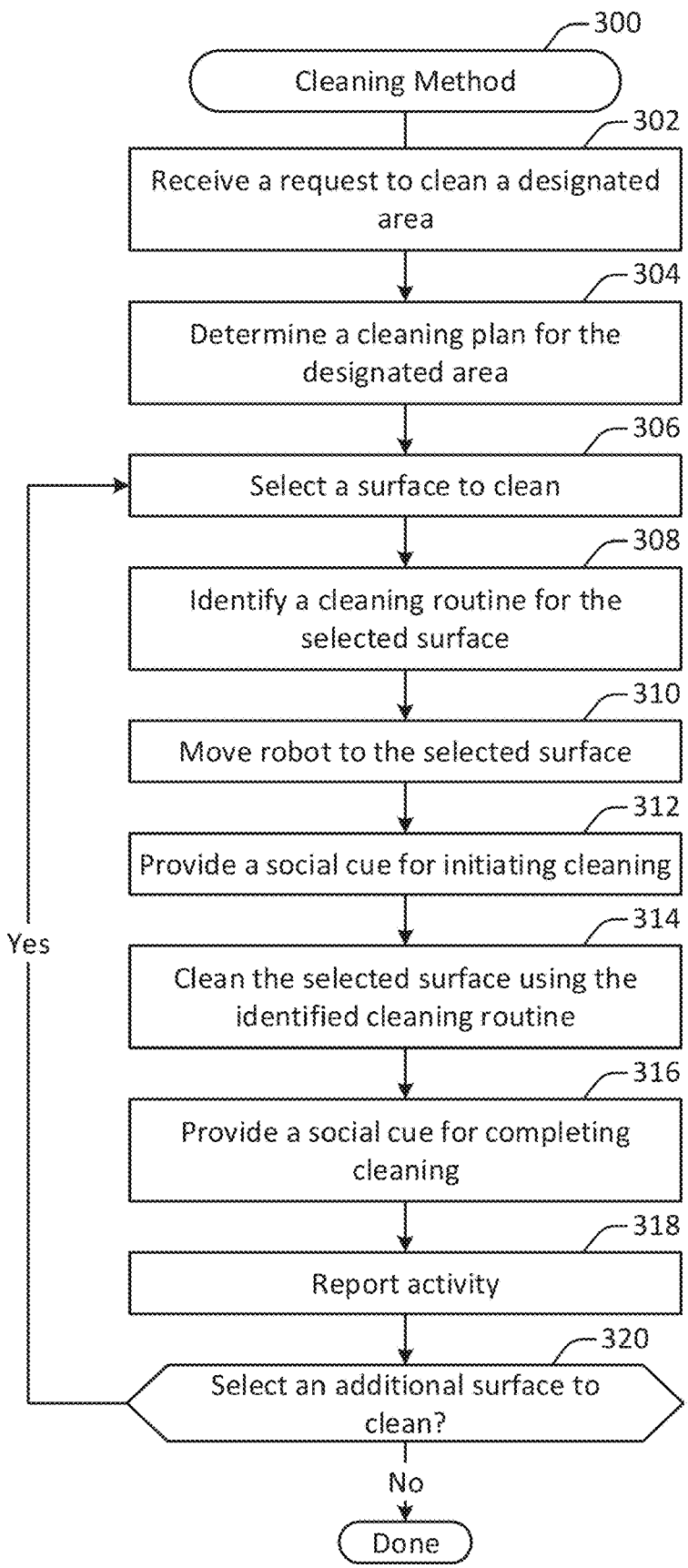
FIG. 3 illustrates a method for cleaning an area, performed in accordance with one or more embodiments.

FIG. 3 illustrates a method 300 for cleaning an area, performed in accordance with one or more embodiments. The method 300 may be performed by a cleaning robot such as the robot 100 shown in FIG. 1. The method 300 may be performed as an example of a task as discussed with respect to the operations 202 and 204 shown in FIG. 2.

A request to clean a designated area is received at 302. According to various embodiments, instructions for where and when to clean can be received from any of multiple sources. For example, a robot may receive instructions from a remote location such as a command center or cleaning service executed on a computing device. As another example, people in an environment may interact with a robot and ask it to perform a cleaning task once or on a regular basis.

According to various embodiments, instructions for where and when to clean can be general or specific. For example, an instruction may specify a particular location and a time at which to clean it. As another example, an instruction may specify a timing constraint associated with a location, such as clean every office door handle in a hallway twice per day. In this case, the robot may develop its own plan and then perform its own execution monitoring.

In some implementations, instructions for where and when to clean can be determined automatically. For example, the cleaning robot may monitor humans as part of its cleaning activity. As part of this monitoring, the cleaning robot may annotate the areas, surfaces, and objects that humans touched, were near to, sneezed on, or otherwise interacted with. Those areas may then be prioritized for cleaning. Human activity may also be determined based on data received from external sensors. For example, a room's motion sensor may indicate that no one has been there, so it may not need to be re-cleaned. As another example, a door sensor may identify a number of people who have visited a room such as a restroom, which may be targeted for recleaning after a threshold number of people have visited the room.

A cleaning plan for the designated area is determined at 304. According to various embodiments, a cleaning plan for a designated area may include, for example, a list of surfaces and/or regions within an area to clean, as well as a path for navigating to each surface and/or region. The cleaning plan may be determined based on any of various considerations, such as the current and predicted location of people within the area, the time required to conduct the cleaning operations, and the distance traveled along the path. For instance, the robot may attempt to first minimize disruption to human activity and then minimize the cleaning time and distance traveled.

A surface to clean is selected at 306. According to various embodiments, the cleaning robot may select a surface to clean based on the cleaning plan at 304. For example, the cleaning robot may attempt to clean each doorknob in a hall or each table in a cafeteria in succession. However, the cleaning robot may adapt its plan in real time to accommodate changes to the environment, such as the actions of people. For example, the cleaning robot may skip a door that is open or a table that is occupied and return the door or table at a later point when it detects that the surface is not in use by humans.

A cleaning routine for the selected surface is identified at 308. According to various embodiments, cleaning different types of objects and surfaces may involve different types of cleaning routines, which may change depending on the type of cleaning conducted. Accordingly, the specific pattern employed may depend on characteristics such as the strength of the UV light, characteristics of the environment, and the level of cleaning desired.

In some implementations, a small planar surface may be cleaned by holding a UV light fixture at a single point above it. A computation may be performed indicating the location of the point and how long the UV fixture needs to remain in place to meet the cleaning goal.

In some implementations, a large planar surface may be cleaned by moving a UV light fixture along a path in an X/Y plane parallel to the surface separated by a fixed distance Z. A computation may be performed to determine the distance Z, the path over the surface, and the speed at which the path is traversed to meet the cleaning goal.

In some implementations, a planar surface may be cleaned by moving a UV light fixture along a path in an X/Y plane parallel to the surface separated by a variable distance Z. For example, near the middle of the surface a higher intensity light may be applied at a larger distance Z, while near the edge of the surface a lower intensity light may be applied at a smaller distance Z to reduce spillover to areas behind the surface. A computation may be performed to determine the variable distance Z, the path over the surface, and the speed at which the path is traversed to meet the cleaning goal.

In some implementations, a surface such as one or more elevator call buttons, one or more internal elevator buttons, and/or small areas around buttons may be cleaned by emitting UV light on a line perpendicular to the plane of the button surface.

In some implementations, non-planar or elongated shape such as a faucet or handle may be cleaned via a vertical scan with a horizontal UV light emission coupled with an arc around the axis of the handle. The trajectory may change depending on the shape of the handle. For example, the robot may have a handle cleaning routine that it can adapt to a particular handle via rotation of a cleaning arm. As another example, spherical knobs may be cleaned via a rotational path around the knob.

According to various embodiments, the cleaning routine for the selected surface may be identified via one or more of a variety of techniques. In some implementations, cleaning routines for a fixed environment may be preprogrammed. For example, a robot may be manually configured to clean different surfaces or objects in an area in particular ways. As another example, a robot may be pre-configured to clean a standardized area such as a chain restaurant building, prefabricated housing area, hotel room, office hallway, retail location, or other such place.

In some implementations, different categories of objects and surfaces may each be associated with a specific cleaning routine. One or more of the cleaning routines may be parameterized. For instance, a procedure for cleaning a planar surface may be parameterized based on the size of the surface. Each object or surface may be pre-categorized by a human in advance. Alternately, or additionally, a trained neural network may be applied to categorize objects based on sensor data.

In some implementations, a cleaning robot may automatically determine a cleaning routine based on sensor data. For example, visual data and/or 3D scanning data may be used to estimate a three dimensional shape of the object or surface to be cleaned. A 3D planner may then be used to plan the trajectory and timing of the cleaning.

In some implementations, a cleaning robot may receive external information such as user input from a person, a two-dimensional or three-dimensional model or drawing of a region, surface, or object, a pre-trained neural network, or other such guidance.

According to various embodiments, a cleaning robot may use any technique in isolation to determine a cleaning plan. Alternately, or additionally, techniques may be used in combination. For example, a cleaning robot may be pre-configured to clean a variety of fixed environments. The cleaning robot may then be configured with specific cleaning routines for specific categories of objects. The cleaning robot may also be capable of automatically determining a cleaning routine based on sensor data, for instance when an object does not fall into an identified category. Finally, the cleaning robot may be configured to clean an object or surface based on user input, for instance when other approaches are insufficient for completing a cleaning task.

The cleaning robot is moved to the selected surface at 310. In some implementations, moving the cleaning robot to the selected surface may involve engaging a mobility mechanism such as one or more wheels or treads. Additionally, the robot may need to navigate around obstacles such as people, animals, objects, or other robots. The robot may conduct that navigation in a socially accommodating manner. For example, the robot may move out of the way of humans, animals, or other robots, even though such accommodation requires moving along a longer path or waiting until a path is clear. As another example, the robot may predict the movement of humans, animals, or other robots in order to plan a path that avoids collisions.

A social cue for initiating cleaning is provided at 312. According to various embodiments, any of a variety of social cues may be employed. Examples of such cues may include, but are not limited to: lights, sounds, vibration, and movement. For example, a robot may activate one or more lights and/or emit one or more sounds when cleaning is initiated. As another example, the robot may activate a spinning mechanical component to provide a visual indicator associated with cleaning.

In particular embodiments, the robot may employ a human communicative apparatus, as discussed with respect to FIG. 1, to execute complex human interactions. For example, a robot may be equipped with a display screen that is coupled with one or more motors. When the robot is actively engaged in ultraviolet cleaning of a surface such as a keyboard, the display screen may display a simulated face. The face may include a visual feature such as sunglasses to indicate that bright light is being emitted by the ultraviolet light source. The motors may be activated to position the display screen so that the face appears to be looking toward the ultraviolet light source, so as to provide a visual cue about the location of the ultraviolet light source via a gaze direction. In addition, the ultraviolet end effector on which the ultraviolet light source may be equipped with one or more visible spectrum lights that are activated during cleaning, which may provide an additional visual cue indicating that ultraviolet light is being emitted. When a human approaches the robot, the robot may take one or more steps to respond. For example, the robot may disable the ultraviolet and visible light sources to show that cleaning has stopped. As another example, the robot may reposition the display screen so that the simulated face appears to gaze at the human, which provides a visual cue that the robot is aware of the human's presence. As yet another example, the robot may change the appearance of the display screen, for instance by removing the sunglasses, presenting a warning symbol and/or message, removing the sunglasses from the simulated face, and/or changing the facial expression displayed on the simulated face. When the human moves away from the robot, the robot may then return the display screen and other components of the human communicative apparatus to the previous state during which cleaning was conducted.

In particular embodiments, a robot may emit a visual social cue indicating how long a task will take. For example, a robot may be equipped with a visible screen that is configured to display one or more countdown clocks. A countdown clock may indicate a time remaining for cleaning a specific surface or object. Alternately, or additionally, a countdown clock may indicate a time remaining for cleaning an entire area. As another example, a cleaning robot may be equipped with one or more colored lights to indicate the degree of completion of a task. For instance, presenting a visual cue may involve changing the color of an LED strip. The visual social cue may be perceivable from a distance so that a human can decide whether to interrupt the robot.

In some embodiments, presenting a visual cue may involve emitting audio. For example, one or more sound effects may be emitted when people transition across virtual boundaries. As another example, audio communication may be emitted in the form of music. As yet another example, audio communication may be emitted in the form of spoken natural language, for instance via text to speech or voice recording. Natural language communication may be presented on a display screen, or through speech, or a combination thereof. As still another example, the cleaning robot may emit a tune or whistle to indicate its progression in a cleaning cycle. As still another example, the cleaning robot may be configured to emit a verbal countdown or other natural language descriptions of progress along a task. For instance, the cleaning robot may state a task and verbally identify the initiation and/or completion of a task.

In some embodiments, presenting a visual cue may involve an information screen configured to display information such as text or icons. For instance, a caution icon may be displayed.

In some embodiments, presenting a visual cue may involve a projector to display information similarly to screen displays. Alternatively, or additionally, a projector may present a visual cue through illumination based on color and/or brightness similarly to LED strips. A projector may be used to show a graphic and/or text on the ground, for instance to indicate a safe boundary for humans to stay away, or onto a surface being disinfected, for instance to display AR information.

In some embodiments, a display screen on the robot may display an emotionally expressive face that is used for indicating system states. For example, when people are detected, the robot may present a happy face. As another example, when people are engaged in interaction for communicating with the robot, the robot may present a face that reflects the situation or statement (e.g., happy, apologetic, or thankful). As yet another example, when the robot predicts that people may soon be in an unsafe location, the robot may display a face indicating shock or panic.

In some embodiments, presenting a visual cue may involve motion. For example, the robot may use its arm for communicative gestures such as pointing to objects or surfaces for confirmation or socially communicating with people, for instance by waving. As another example, the robot may have the ability to move a "head" area (e.g., with 1-3 degrees of freedom) on which a display screen is mounted to control head gaze for communicating with people and directing sensors. Head gaze direction may be used to communicate task state (e.g., navigational goals, object/surface targets for disinfection) or interaction state (e.g., people being interacted with). Neck motions may also be used as communicative gestures, such as shaking the head no. As yet another example, the robot may use a mobile base trajectory for communication, for instance by driving to encircle a region to refer to it for task confirmation. As still another example, any of the robot's movable components may be used for emphasis within a communicative message, for instance for beat gestures.

The selected surface is cleaned using the identified cleaning routine at 314. In some implementations, cleaning the selected surface may involve operations such as adjusting the position of the cleaning robot, adjusting the position of one or more cleaning devices, and/or adjusting one or more settings associated with a cleaning device such as the intensity of UV light emitted. For instance, a UV light may be activated and strengthened or weakened in intensity as it is moved through space in an arc around a circular object or in a plan over a flat object.

A social cue for completing cleaning is provided at 316. In some implementations, the social cue for completing cleaning may simply involve no longer emitting the social cue for initiating cleaning provided at 312. Alternately, or additionally, a different social cue may be emitted to demonstrate that cleaning has stopped. For instance, a robot may emit a green light when not cleaning and a red light while cleaning.

In particular embodiments, a cleaning robot may strategically determine a social cue based on factors such as environmental characteristics. For example, the cleaning robot may emit a brighter light or louder sound in a brighter or louder environment with more people, while emitting a dimmer light or quieter sound in a darker or quieter environment.

Activity is reported at 318. According to various embodiments, the activity may be reported via the communication interface 106 shown in FIG. 1. The cleaning robot may report on any or all activity. For example, the cleaning robot may report on cleaning activity such as where it cleaned, when it cleaned, and/or one or more parameters of the cleaning process. As another example, the cleaning robot may report on social accommodation actions such as when, where, why, and how it took action to accommodate activity by humans, animals, or other robots. As yet another example, the cleaning robot may report on characteristics of the environment observed via its sensors, such as the presence or absence of trash, graffiti, or damage. As still another example, the cleaning robot may report on successes, failures, and/or reasons for failure while executing its cleaning plan.

In some implementations, activity may be reported in real time. For example, a robot may communicate with a remote database via WiFi. Alternatively, or additionally, activity may be reported via bulk communication. For example, a robot may transmit a comprehensive log of activity, for instance via a wired connection, when the robot returns to a charging or docking station.

A determination is made at 320 as to whether to select an additional surface to clean. In some implementations, the determination may be made at least in part on whether the cleaning robot has cleaned each surface according to the cleaning plan determined at 102. For instance, the cleaning robot may revisit a surface that it was initially unable to clean due to accommodating people within the environment.

In particular embodiments, one or more of the operations shown in FIG. 3 may be omitted. For example, the cleaning robot may not provide a social cue in some configurations, such as in settings where limited light and sound disruption is desired.

Figure 4:
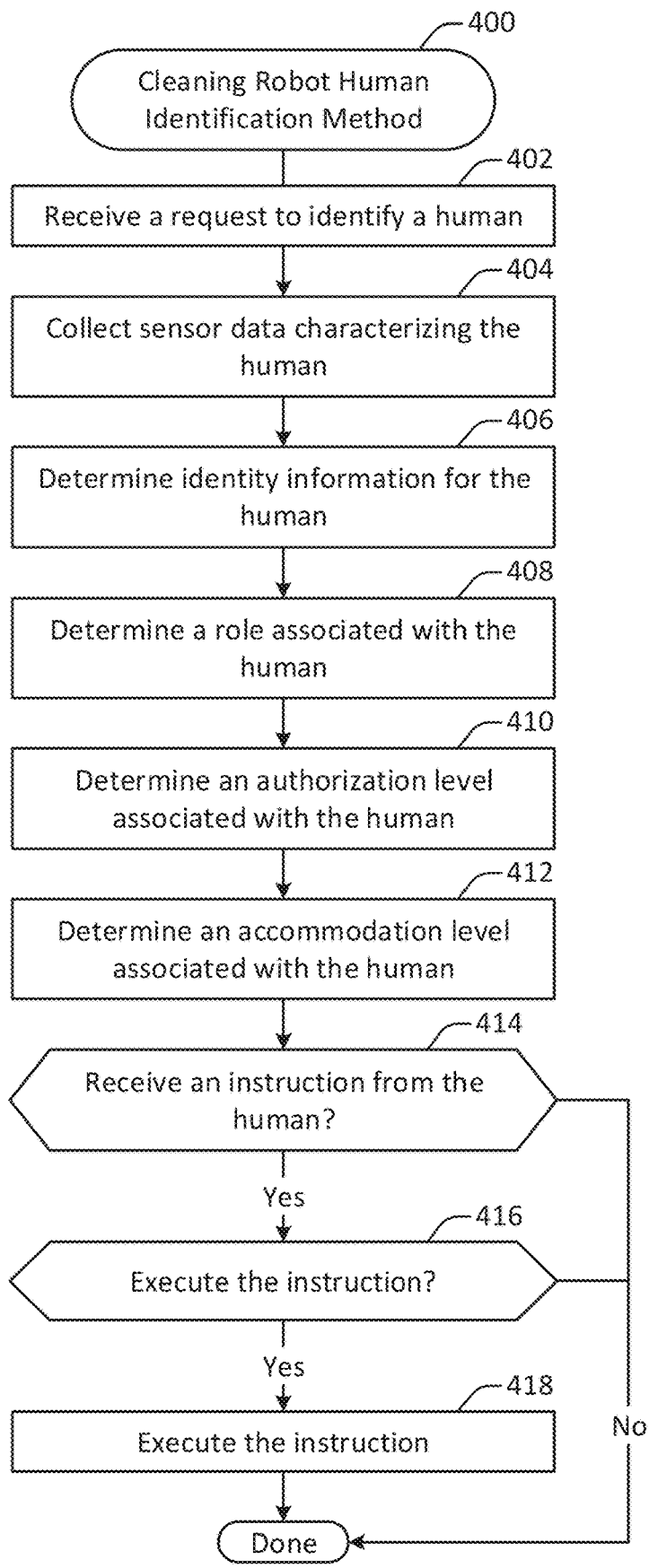
FIG. 4 illustrates a method for human identification by a cleaning robot, performed in accordance with one or more embodiments.

FIG. 4 illustrates a method 400 for human identification by a cleaning robot, performed in accordance with one or more embodiments. The method 400 may be performed by the cleaning robot as part of, or in addition to, the execution of any other operations. For example, the method 400 may be performed by the cleaning robot as it is navigating an environment, performing social accommodation, and/or executing a cleaning task. As another example, the method 400 may be an example of a social disruption as discussed with respect to the operations 208, 210, 212, and 214 in the method 200 shown in FIG. 2.

A request to identify a human is received at 402. According to various embodiments, the request may be generated automatically, for instance whenever a human comes within a designated range of the cleaning robot. Alternatively, or additionally, the request may be generated when an event is detected. For instance, the request may be generated when a human instructs the robot to perform a task.

Sensor data characterizing the human is collected at 404. According to various embodiments, various types of sensor data may be collected. For example, visual data such as video footage and/or one or more still images may be collected from a camera. As another example, an RFID sensor, barcode, or other such data may be read from an ID badge associated with the human.

When possible, identity information for the human is determined at 406. In some implementations, the identity information may be determined at least in part by querying a remote database. For example, an image of a human may be used to query a remote database that links such images with information such as name and role. As another example, an ID barcode or RFID code may be used to query such a database.

A role associated with the human is determined at 408. In some embodiments, when available, the role may be determined directly from the identity information determined at the operation 406. Alternatively, or additionally, role information may be determined based on contextual cues. For example, a doctor or nurse in a hospital setting may be identified based on the presence of clothing or medical equipment. As another example, an employee or manager in an office, industrial, or retail setting may be identified based on clothing or insignia. As yet another example, individuals having a particular role may carry a special identifier such as an RFID tag on a badge.

An authorization level for the human is determined at 410. In some implementations, the authorization level may characterize the type of instructions that the human is authorized to give to the robot. For instance, a robot may be configured to act on any instructions from a designated maintenance operator. At the same time, the robot may be configured to act on a limited set of instructions from authorized persons such as doctors and nurses in a hospital, employees in an office setting, or managers in an industrial setting. The robot may be configured to ignore instructions from unauthorized individuals.

An accommodation level associated with the human is determined at 412. According to various embodiments, the accommodation level may indicate a level of deference afforded to the human. For example, in a hospital setting, the cleaning robot may be configured to give doctors and nurses a wide berth, while affording less deference to the general public.

At 414, a determination is made as to whether an instruction is received from the human. At 416, if an instruction is received, a determination is made as to whether to execution the instruction, for instance based on the human's authorization level. If the decision is made to execute the instruction, then at 418 the instruction is executed.

According to various embodiments, the instruction could be any instruction within the robot's command set. For example, the human could instruct the robot to start or stop cleaning an area. As another example, the human could instruct the robot to move or stop moving. As yet another example, the human could instruct the robot to pause a task.

According to various embodiments, the robot may be configured to receive user input in any of a variety of ways. For example, a human may employ natural language to command the robot. Voice input may be provided to a microphone located on the robot, and/or through voice or typed text on a mobile phone, web application, or desktop application.

In some implementations, the robot may be configured to receive user input via hand gestures, for instance to facilitate contact-less interaction in noisy environments where speech recognition may be less accurate. Such gestures may be used for operations such as engaging or disengaging the robot, instructing it to start or stop tasks, providing yes or no answers, navigating a menu associated with the robot, pointing at regions or objects in the real world, making movements relative to a screen displaying visual information, or a variety of other gestures.

In some implementations, user input with the robot may be provided based on a remote user interface, for instance via a mobile phone, web application, or desktop application. In this way, a user may instruct and communicate with the robot when not co-present with it. Such interaction may take place via a graphical user interface, via spoken voice commands (e.g., a voice-based phone call), via a video call, or a combination thereof. When a user is co-present with the robot, information from a mobile device may be referenced during face-to-face interaction, and the mobile device used as an additional input device.

In some implementations, user input with the robot may be provided via near-field communication. For example, a user may authenticate or provide other information via an RFID badge.

In particular embodiments, touch-based user input may be used. Examples of such input may include, but are not limited to, touching options on a screen, pressing buttons, or activating touch sensors. For example, the robot may have capacity and/or resistive touch sensors on the surface of its body. As another example, the robot may have torque sensing at joints, which may help to detect contact for a variety of reasons (e.g., safety).

Figure 5:
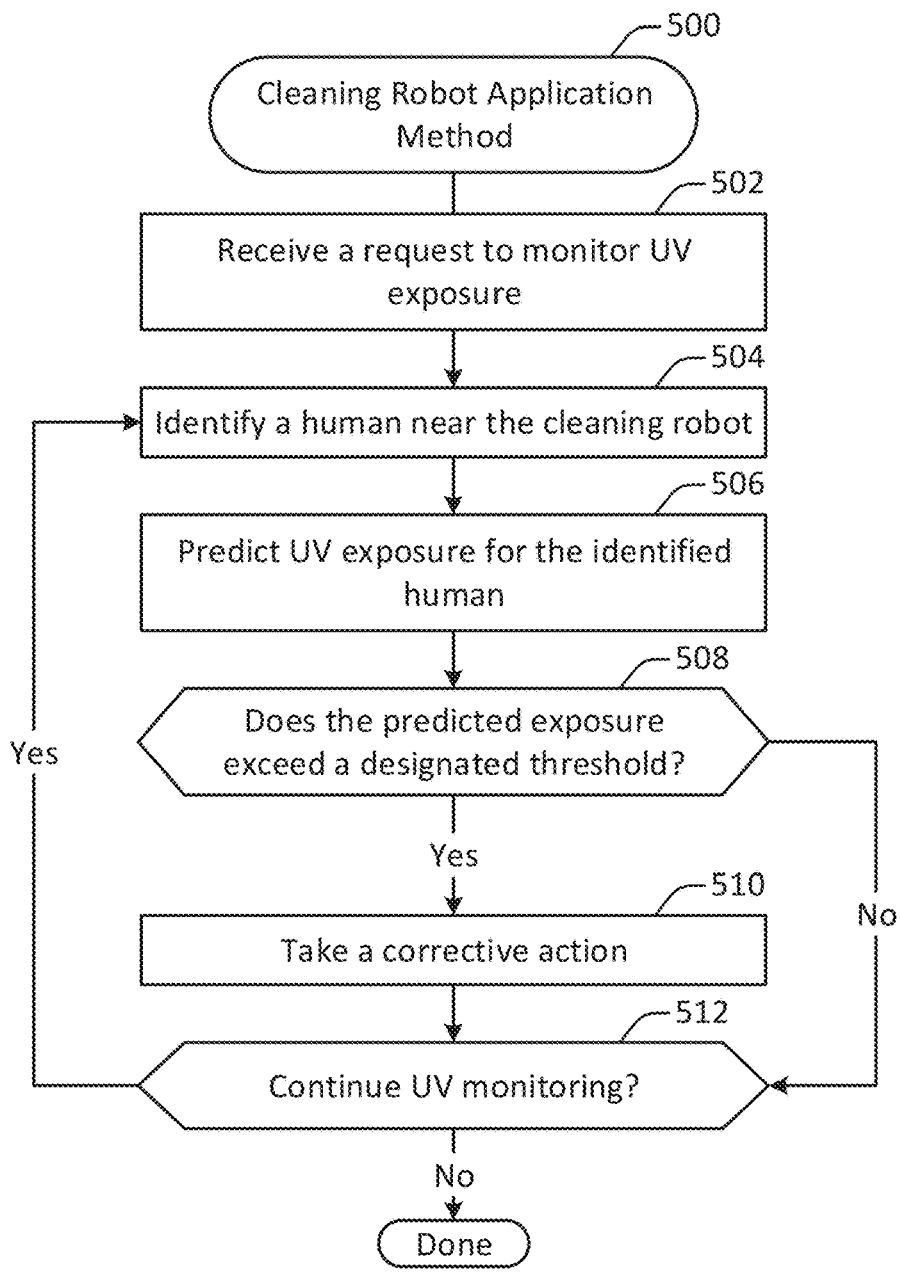
FIG. 5 illustrates a method for UV application, performed in accordance with one or more embodiments.

FIG. 5 illustrates a method 500 for UV application, performed in accordance with one or more embodiments. UV light is harmful not only to bacteria, viruses, and fungi, but also to people and animals. At moderate to high levels of intensity, skin and eye protection is required for direct exposure. According to various embodiments, the method 500 may be performed by a cleaning robot concurrently with the performance of other methods, such as the methods shown in FIG. 2, FIG. 3, and FIG. 5.

A request to monitor UV exposure is received at 502. According to various embodiments, the request may be generated automatically, for instance when a robot moves into a new area or begins a cleaning cycle. Alternatively, or additionally, the request may be generated based on user input, for instance when a human instructs the robot to monitor for UV exposure. As still another possibility, the request may be generated when a designated event is detected, such as when the density and/or proximity of people to the cleaning robot exceeds a designated threshold.

At 504, a human near the cleaning robot is identified. As discussed with respect to the method 500 shown in FIG. 5, the cleaning robot may employ any of a number of techniques to identify humans. Further, in some configurations such techniques may be extended to encompass animals.

At 506, UV exposure for the identified human is estimated. According to various embodiments, the robot may estimate the UV exposure for the identified human by maintaining a 3D map of instantaneous intensity based on reflectivity of surfaces in the vicinity. Reflectivity data may be pre-configured, received from a remote server, or determined by the cleaning robot itself, for instance via a visible or infrared camera. Reflectivity data, in combination with computational models of UV intensity, allows for the calculation of a dosage estimate for each human. In general, the dramatic reduction of UV intensity with distance may mean that the cleaning robot need only calculate and maintain dosage estimates for humans that are located within a designated distance (e.g., 5 meters) of the cleaning robot while the UV light is activated.

Figure 22:
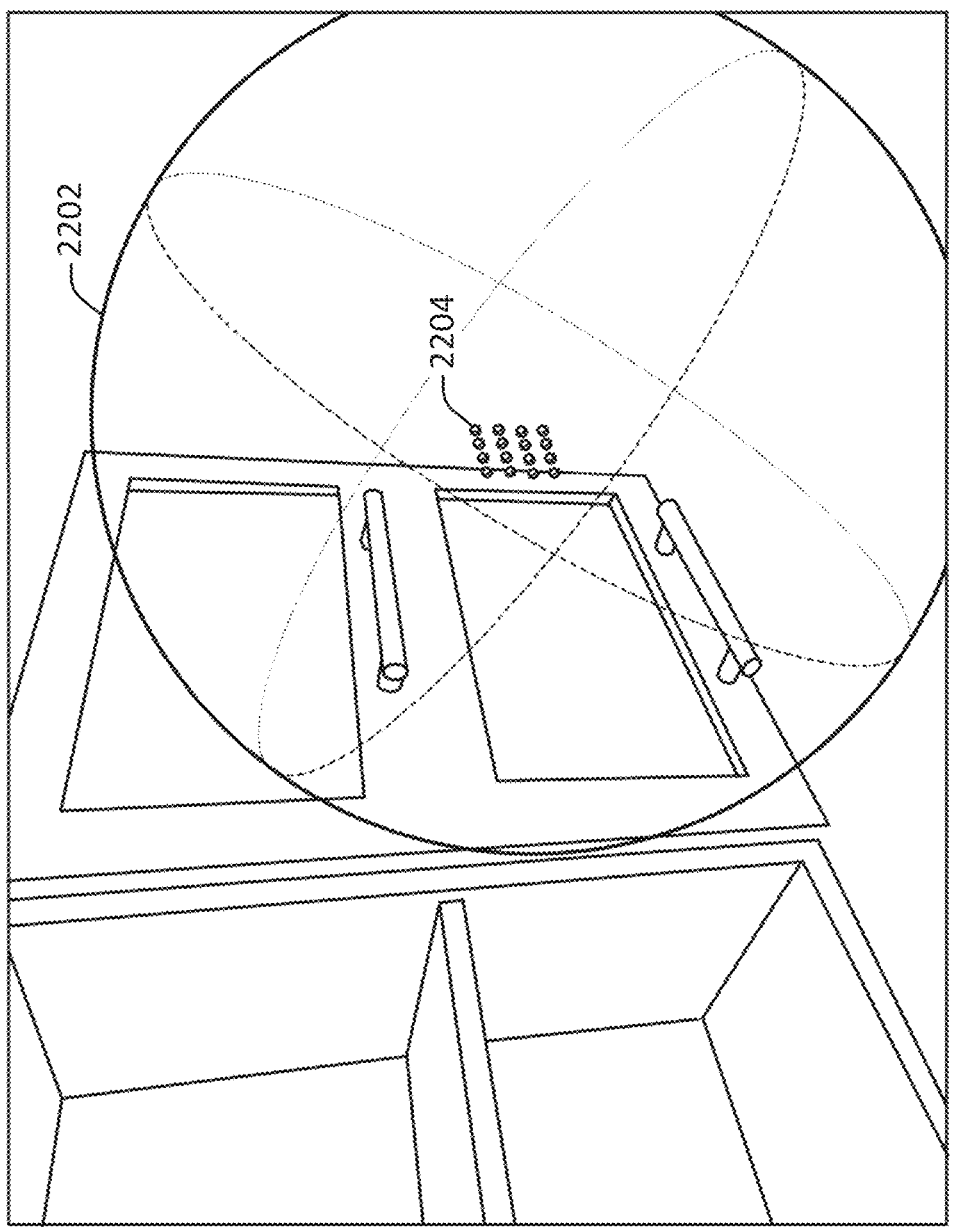
FIGS. 22, 23, and 24 illustrate exposure models, generated in accordance with one or more embodiments.

In particular embodiments UV exposure for the identified human may be estimated based on a three-dimensional model of a space in which a human is located. An example of such a model is shown in FIG. 22, where a sphere of exposure 2202 is estimated around an array of UV light sources 2204. The sphere expands over time as the UV light sources continue to operate in accordance with an exposure model, such as those described with respect to FIGS. 9A and 9B. A similar approach may be used to estimate the dose received by a surface. In this way, the robot can ensure that a surface is cleaned by ensuring that the surface receives a dosage exceeding a first threshold while at the same time ensuring that humans are not exposed to UV radiation exceeding a second threshold.

In particular embodiments, a surface or object may be modeled as a mesh of vertices. The dose for a surface or object may then be estimated for each vertex of the surface or object. The surface or object is then determined to have received a sufficiently high dose when all vertices have received a dose exceeding a designated threshold.

Figure 23:
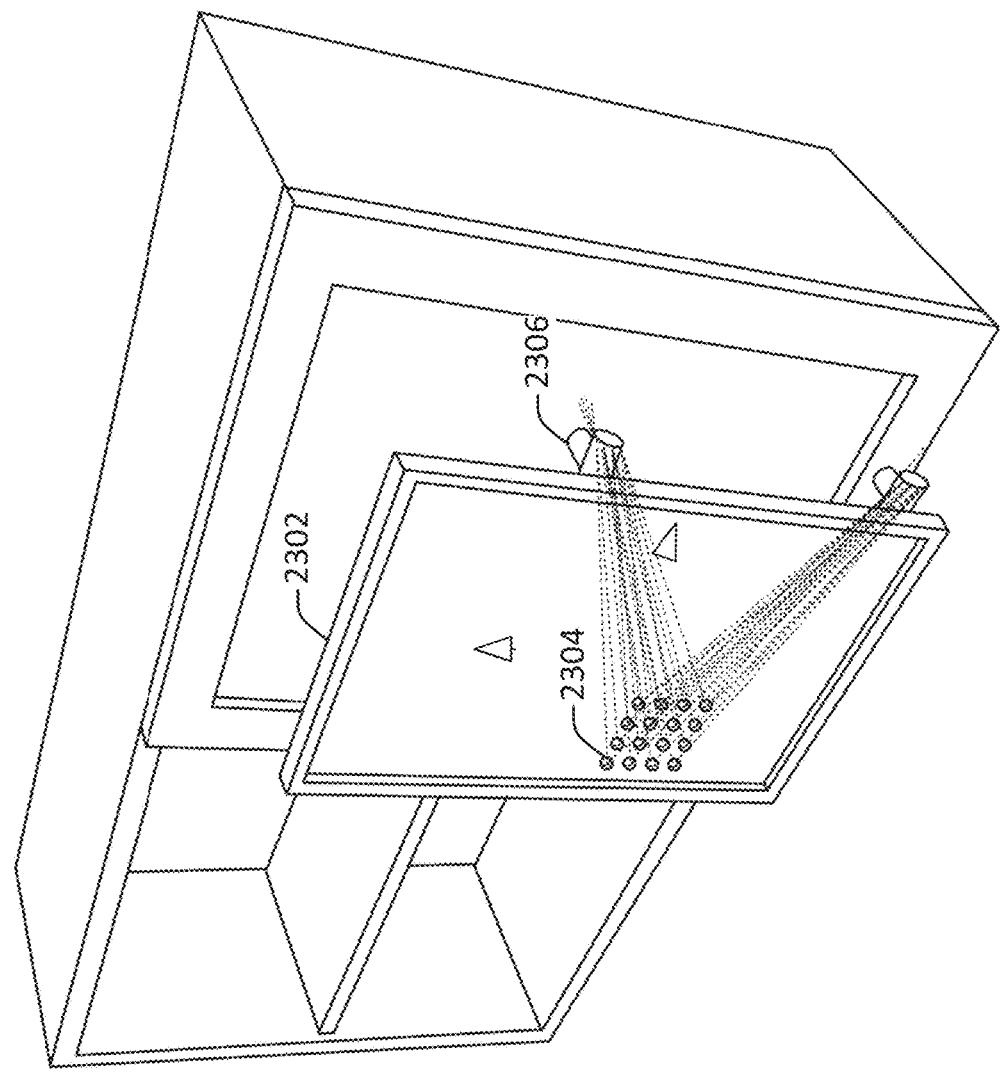
Figure 24:
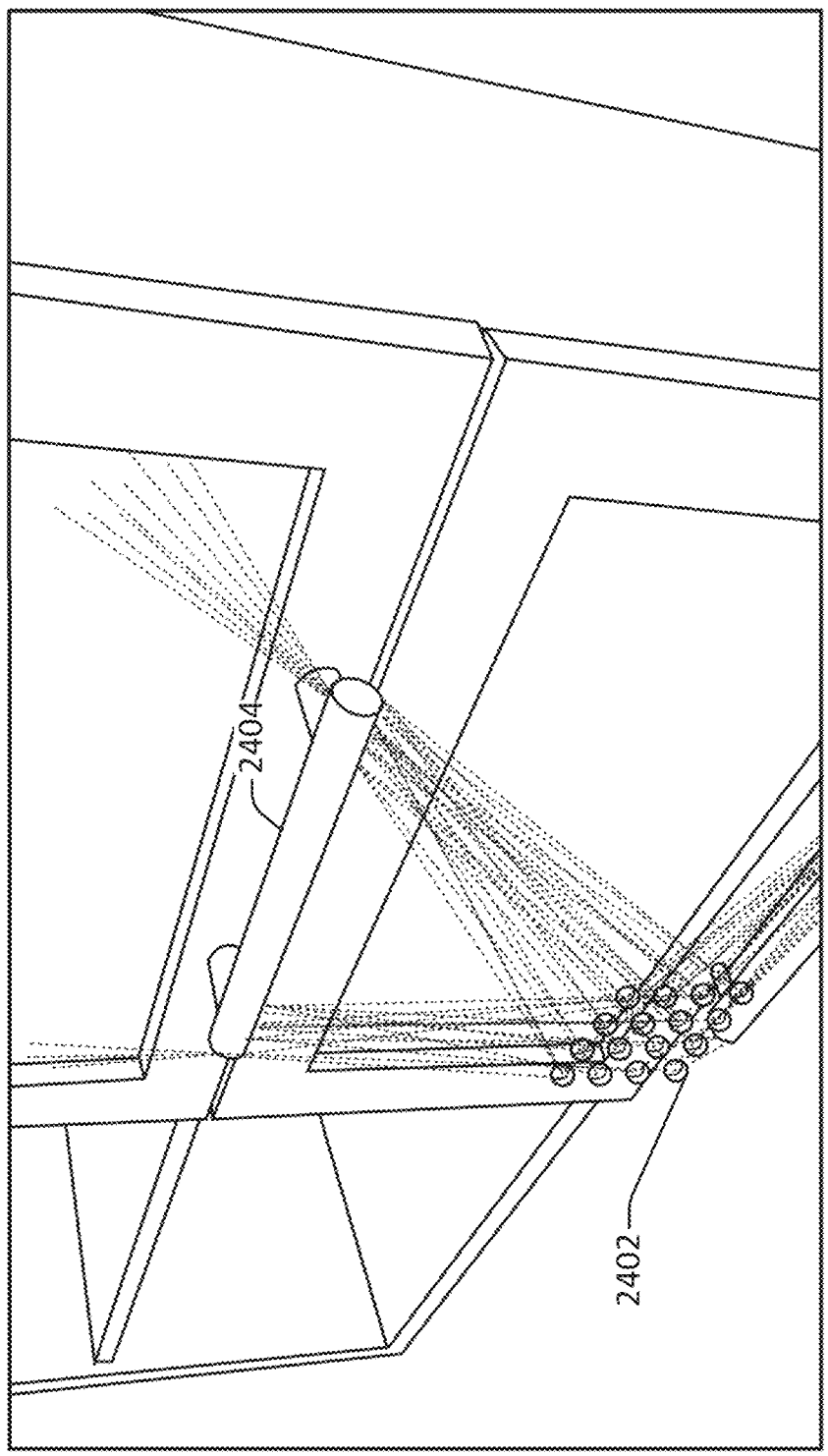

In particular embodiments, occlusions may be modeled with ray tracing as the light source, the object being cleaned, and/or one or more objects within the environment move. In this way, the dose received by an object or surface and/or the exposure received by a human may be more accurately modeled. An example of such an approach is shown in FIG. 23, where the plane 2302 represents a surface that has moved between the UV light array 2304 and the handle of the cabinet 2306. In particular embodiments, ray tracing may also be used to model the field of view of the light source. For example, in FIG. 23, ray tracing has been used to estimate UV exposure at different parts of the cabinet handle 2360. Another example of such an approach with a light source having a 130-degree field of view is shown in FIG. 24, in which the UV array 2402 is projecting light onto the front and bottom of the handle 2404.

In particular embodiments, the exposure for the human and/or the dosage for the surface or object may be periodically transmitted to a remote location such as a database system via wireless communication. The cleaning robot may also receive data on exposure from the remote location. In this way, an accurate exposure level for a human may be estimated even when a human is near more than one cleaning robot during a period of time.

At 508, a determination is made as to whether the estimated dosage exceeds a designated threshold. Typical guidelines for human exposure advice not receiving any exposure of more than 3 to 5 mJ/cm$^2$, that is, not to receive an exposure of more than 0.01 to 0.02 µW/cm$^2$ for more than 8 hours. However, a different (e.g., substantially more conservative) threshold may be employed out of an abundance of caution.

If the dose is predicted or measured to exceed safety thresholds is exceeded, then at 510 a corrective action is taken. According to various embodiments, the detection of a human dosage in excess of the threshold may be treated in a manner similar to a social disruption as discussed with respect to the method 200 shown in FIG. 2. For example, the human experiencing a dosage in excess of the threshold may be notified via a visible alert, an audible alert, and/or a message such as an email or text message. As another example, the cleaning robot may cease cleaning until the human is no longer in the area. As yet another example, the cleaning robot may cease cleaning and move to a different area where the human is not present. At 512, a determination is made as to whether to continue UV monitoring.

Figure 6:
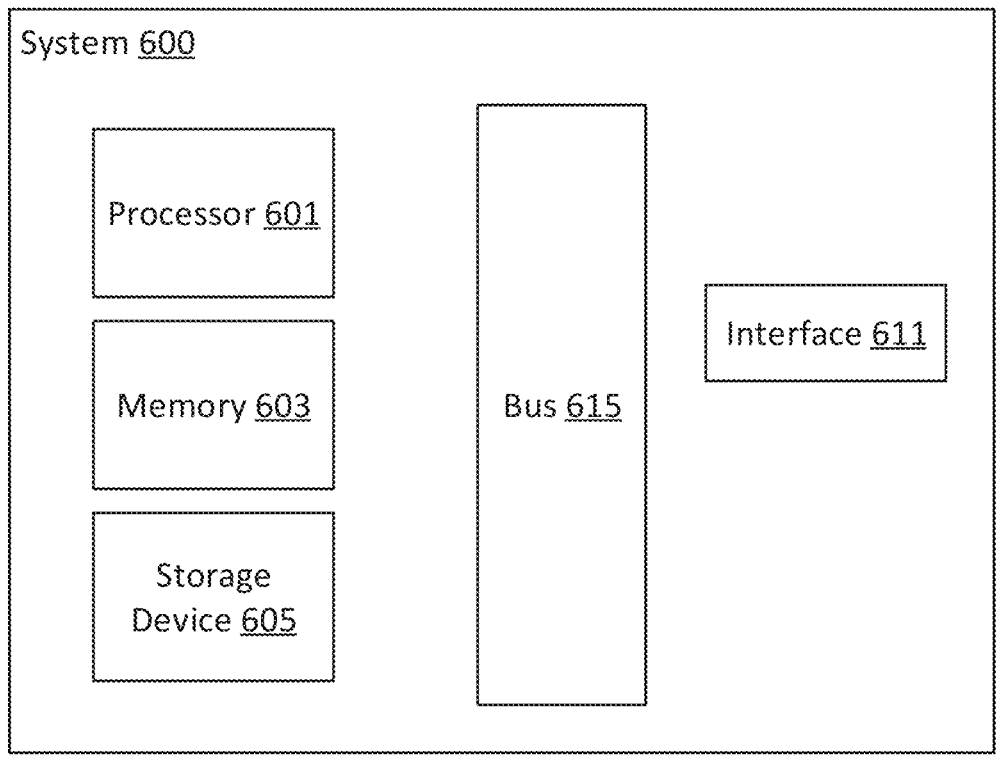
FIG. 6 illustrates one example of a computing device.

FIG. 6 illustrates one example of a computing device. According to various embodiments, a system 600 suitable for implementing embodiments described herein includes a processor 601, a memory module 603, a storage device 605, an interface 611, and a bus 615 (e.g., a PCI bus or other interconnection fabric.) System 600 may operate as variety of devices such as cleaning robot, remote server, or any other device or service described herein. Although a particular configuration is described, a variety of alternative configurations are possible. The processor 601 may perform operations such as those described herein. Instructions for performing such operations may be embodied in the memory 603, on one or more non-transitory computer readable media, or on some other storage device. Various specially configured devices can also be used in place of or in addition to the processor 601. The interface 611 may be configured to send and receive data packets over a network. Examples of supported interfaces include, but are not limited to: Ethernet, fast Ethernet, Gigabit Ethernet, frame relay, cable, digital subscriber line (DSL), token ring, Asynchronous Transfer Mode (ATM), High-Speed Serial Interface (HSSI), and Fiber Distributed Data Interface (FDDI). These interfaces may include ports appropriate for communication with the appropriate media. They may also include an independent processor and/or volatile RAM. A computer system or computing device may include or communicate with a monitor, printer, or other suitable display for providing any of the results mentioned herein to a user.

Any of the disclosed implementations may be embodied in various types of hardware, software, firmware, computer readable media, and combinations thereof. For example, some techniques disclosed herein may be implemented, at least in part, by non-transitory computer-readable media that include program instructions, state information, etc., for configuring a computing system to perform various services and operations described herein. Examples of program instructions include both machine code, such as produced by a compiler, and higher-level code that may be executed via an interpreter. Instructions may be embodied in any suitable language such as, for example, Java, Python, C++, C, HTML, any other markup language, JavaScript, ActiveX, VBScript, or Perl. Examples of non-transitory computer-readable media include, but are not limited to: magnetic media such as hard disks and magnetic tape; optical media such as flash memory, compact disk (CD) or digital versatile disk (DVD); magneto-optical media; and other hardware devices such as read-only memory ("ROM") devices and random-access memory ("RAM") devices. A non-transitory computer-readable medium may be any combination of such storage devices.

Figure 7:
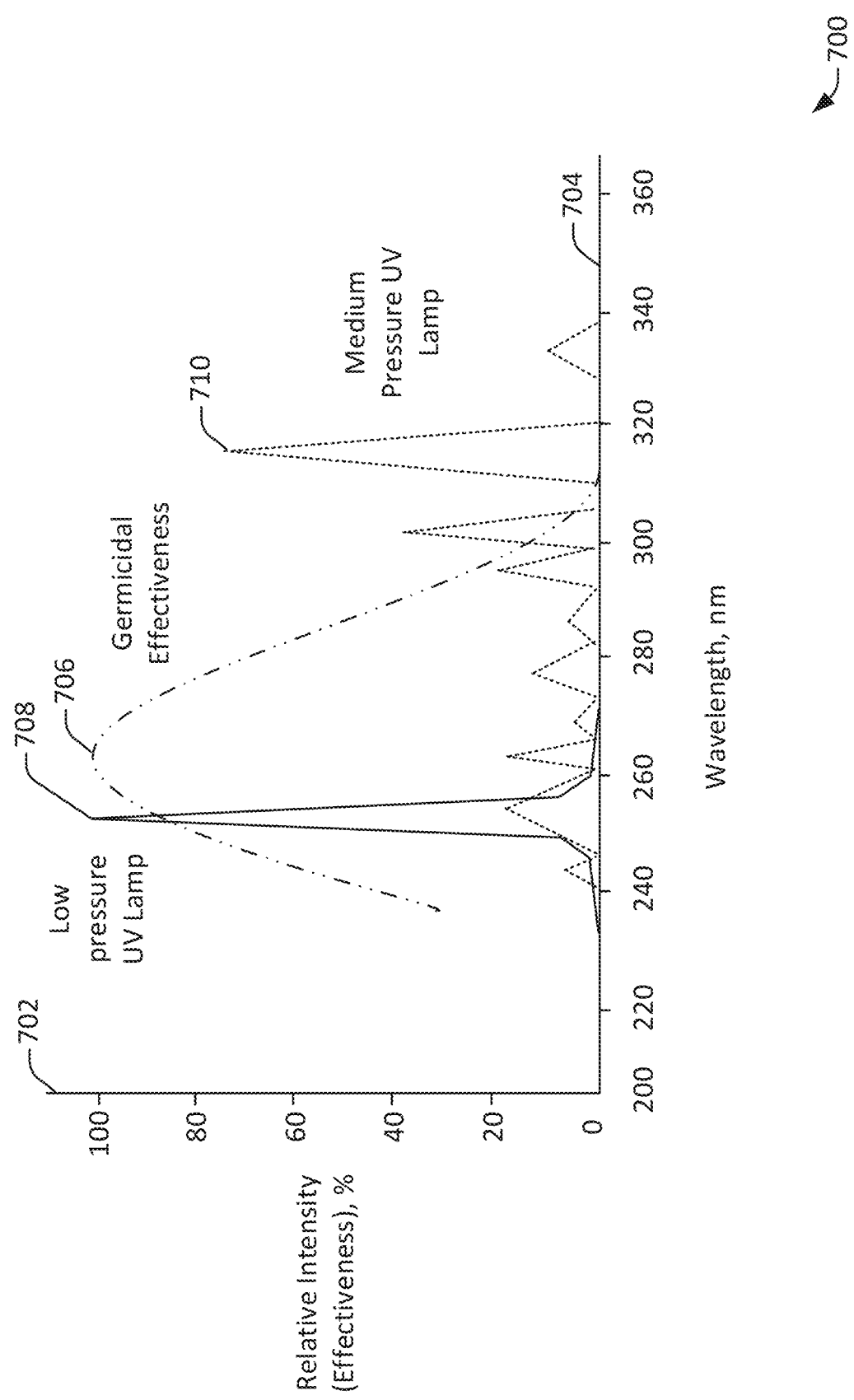
FIG. 7 illustrates a plot generated in accordance with one or more embodiments.

FIG. 7 illustrates a plot 700 generated in accordance with one or more embodiments. The X-axis 704 represents light wavelength in nanometers and the Y-axis 702 represents relative intensity. Germicidal effectiveness peaks at a wavelength 706 of approximately 265 nanometers, at which point most bacteria, viruses, and fungi tend to absorb the most energy. Low pressure UV lamps are highly efficient at generate light at wavelength 708 of approximately 254 nanometers, whereas medium pressure UV lamps 710 generate light across a broader spectrum but have lower relative intensity. Low pressure UV lamps also operate at a lower temperature and thus are generally considered to be safer than high pressure UV lamps.

According to various embodiments, various types of light sources may be used for emitting UV light. For example, fluorescent UV lights generate UV light via a plasma by running current through noble gases such as argon, neon, xenon and helium. Florescent lights require a significant amount of power, typically last more than 10,000 hours, generate light at a wavelength of approximately 254 nanometers, as well as the 185 nanometers region for ozone producing models, and often require a 1-5 minute start-up time. LED lights generate UV light by exciting a diode in a fashion similar to a LASER. LED lights have lower power requirements, typically last between 2,000 and 10,000 hours, can be turned on and off instantly, and have lower power requirements.

Figure 8:
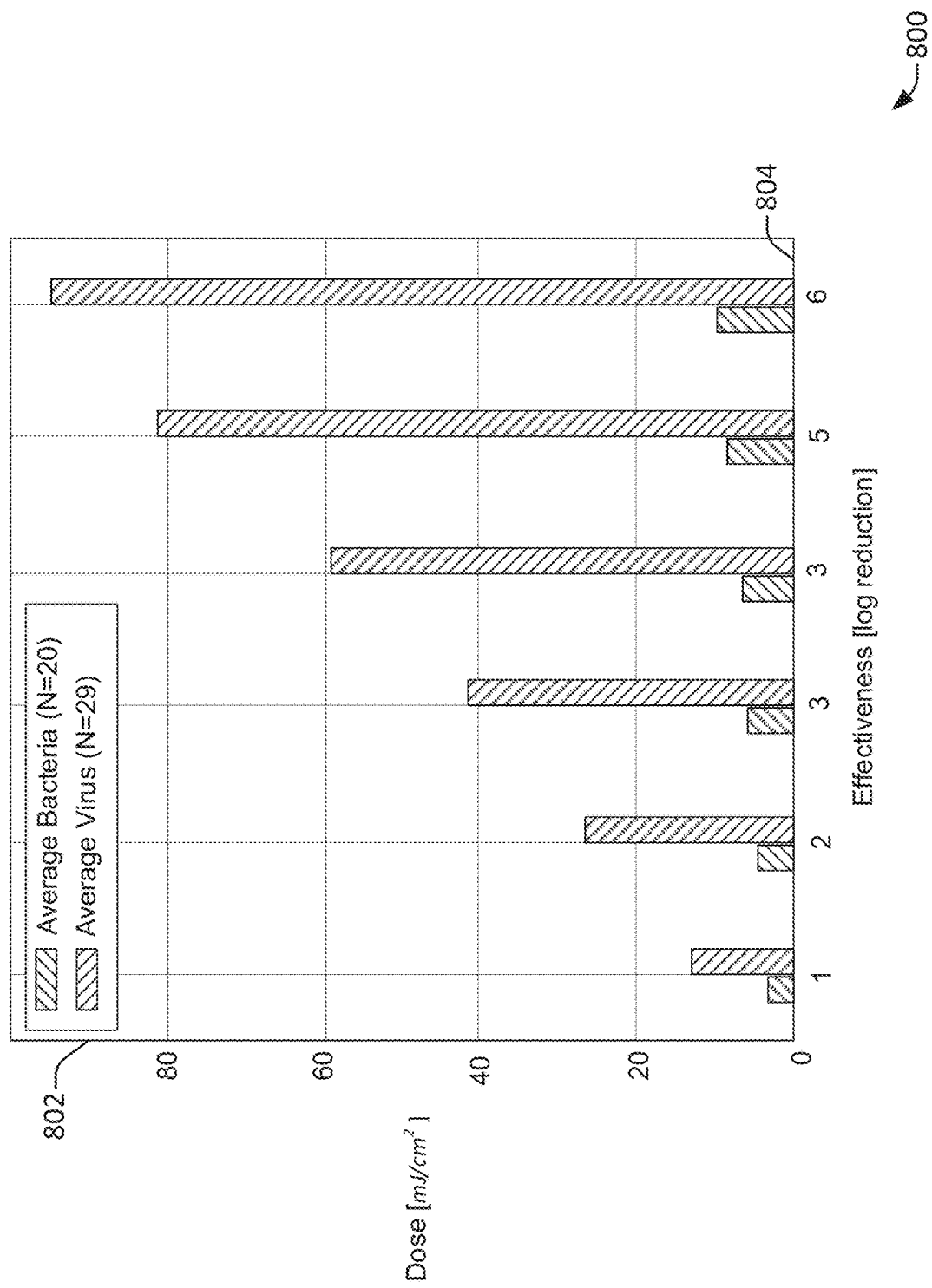
FIG. 8 illustrates a plot generated in accordance with one or more embodiments.

FIG. 8 illustrates a plot 800 generated in accordance with one or more embodiments. The Y-axis 802 represents the dose received, which represents the amount of energy received by a surface over time and which is measured in millijoules per square centimeter (mJ/cm$^2$). The X-axis 804 represents the effectiveness measured as the log (base 10) reduction in count. On average, fungi are more resistant to UV radiation than viruses, which are more resistant to UV radiation than bacteria. In FIG. 8, rendering inactive 99.9% of bacteria and viruses requires a dose of approximately 42 mJ/cm$^2$ for viruses and a dose of approximately 7 mJ/cm$^2$ for bacteria. Similarly, rendering inactive 99.9999% of bacteria and viruses requires a dose of approximately 93 mJ/cm$^2$ for viruses and a dose of approximately 9 mJ/cm$^2$ for bacteria. Typical thresholds for testing the efficacy of disinfectants are 3-log (99.9% inactivated) and 6-log (99.9999% inactivated).

Figure 9B:
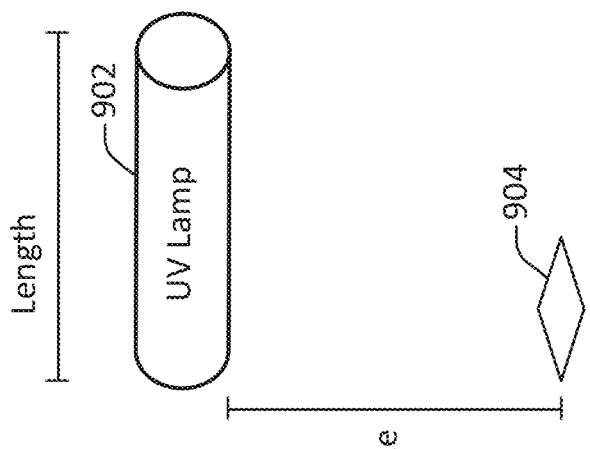
FIG. 9A and FIG. 9B illustrate models for light source intensity according to one or more embodiments.
Figure 9A:
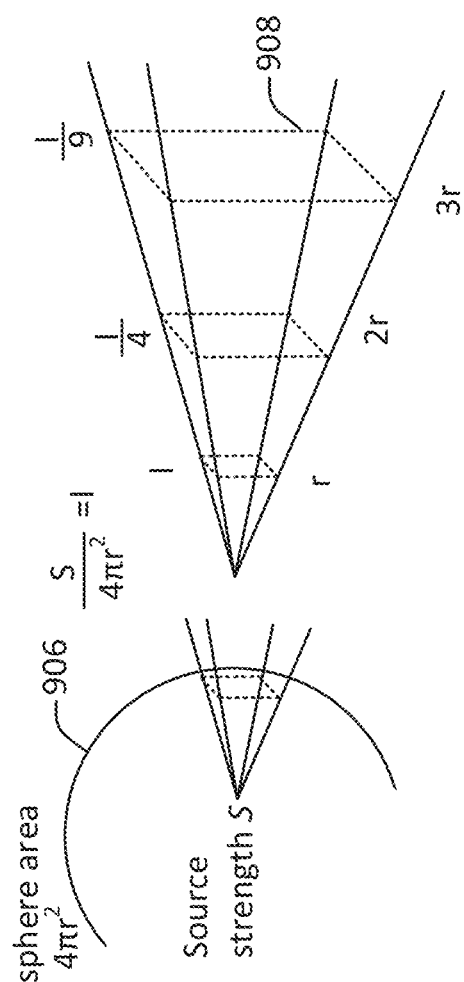

In some implementations, the energy received by microbes, people, or animals may be modeled via a point source model, illustrated in FIG. 9A, which is most effective at approximating small, uniform sources. In the point source model, the intensity at a virtual sphere surrounding the point is measured as the surface of the area divided by the area of the sphere 906, which is $4\pi r^2$. Because the energy twice as far from the source is spread over four times the area, the energy received in the same area 908 is one-fourth the intensity.

In some implementations, the energy received by microbes, people, or animals may be modeled via a field intensity model, illustrated in FIG. 9B, which is most effective at approximating tube-shaped sources. In FIG. 9B, a UV Lamp 902 of a certain length is positioned a particular distance away from a surface 904.

Figures 10A, 10B:
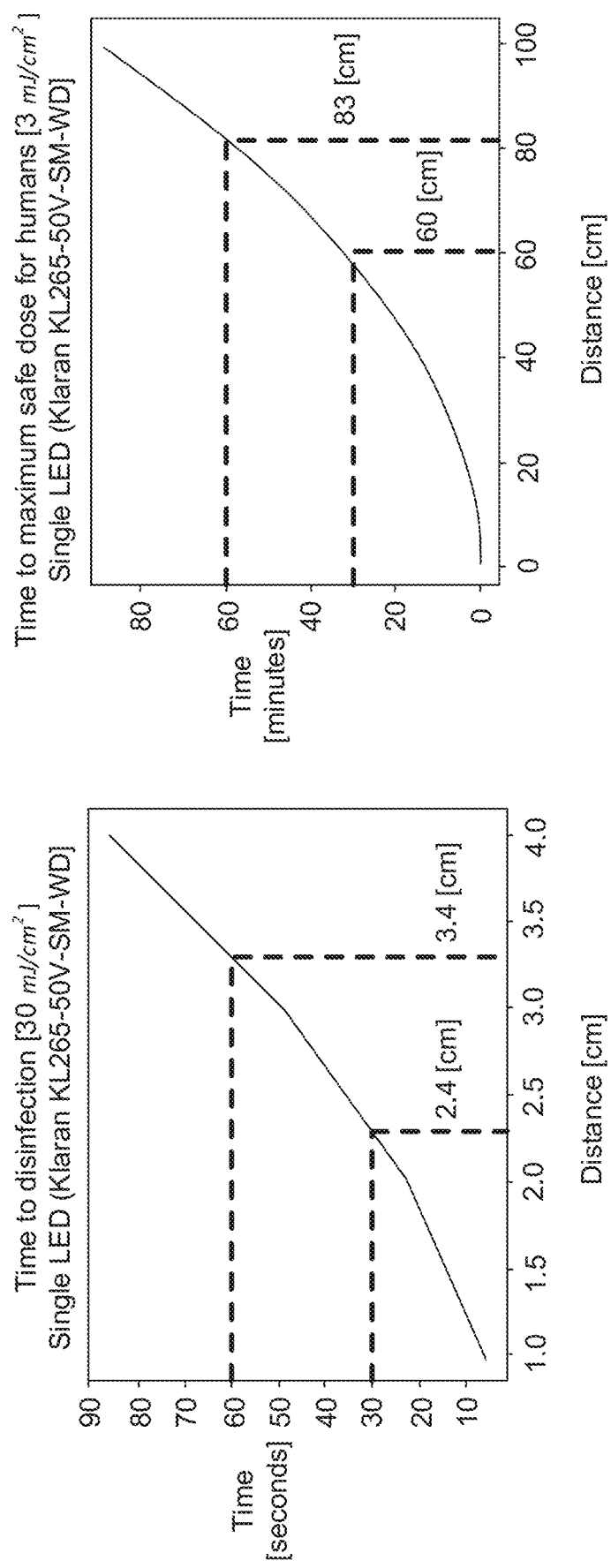
FIG. 10A and FIG. 10B illustrate plots generated in accordance with one or more embodiments determined based on the point source model.

FIG. 10A and FIG. 10B illustrate plots 1000 and 1050 generated in accordance with one or more embodiments determined based on the point source model. FIG. 10A plots the time in seconds for a 3-log reduction at a dose of 30 mJ/cm$^2$ at various distances from the target. The distance is 2.4 cm for a 30 second exposure and 3.4 cm for a 60 second exposure. FIG. 10B plots the time in minutes to a maximum safe dose for a human of 3 mJ/cm$^2$ at various distances from the target. The time is approximately 30 minutes for a distance of 60 cm and approximately 60 minutes for a distance of 83 cm.

Figure 11B:
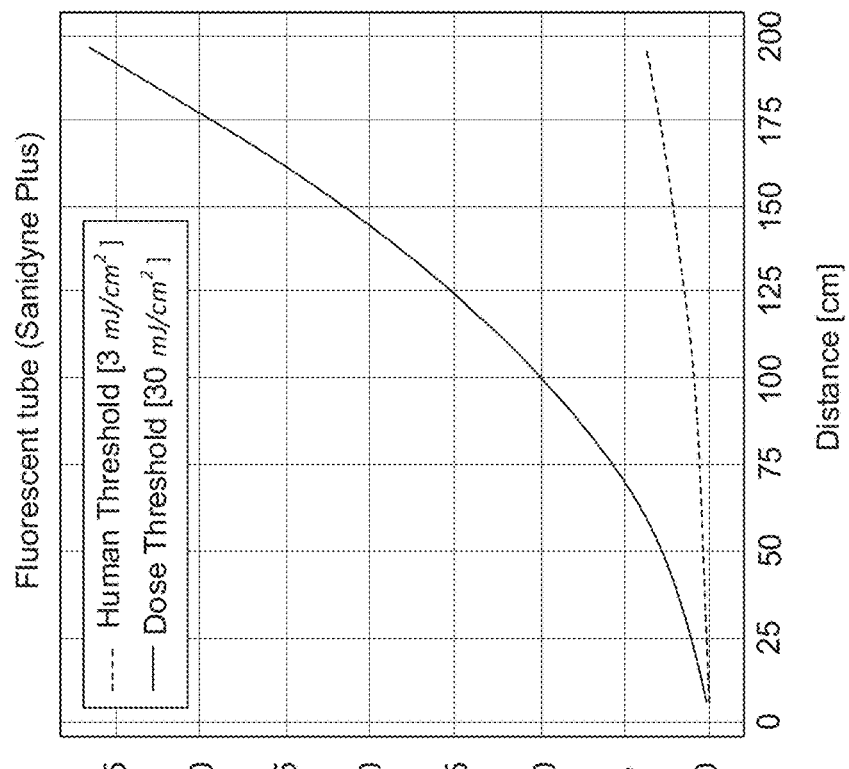
Figure 11A:
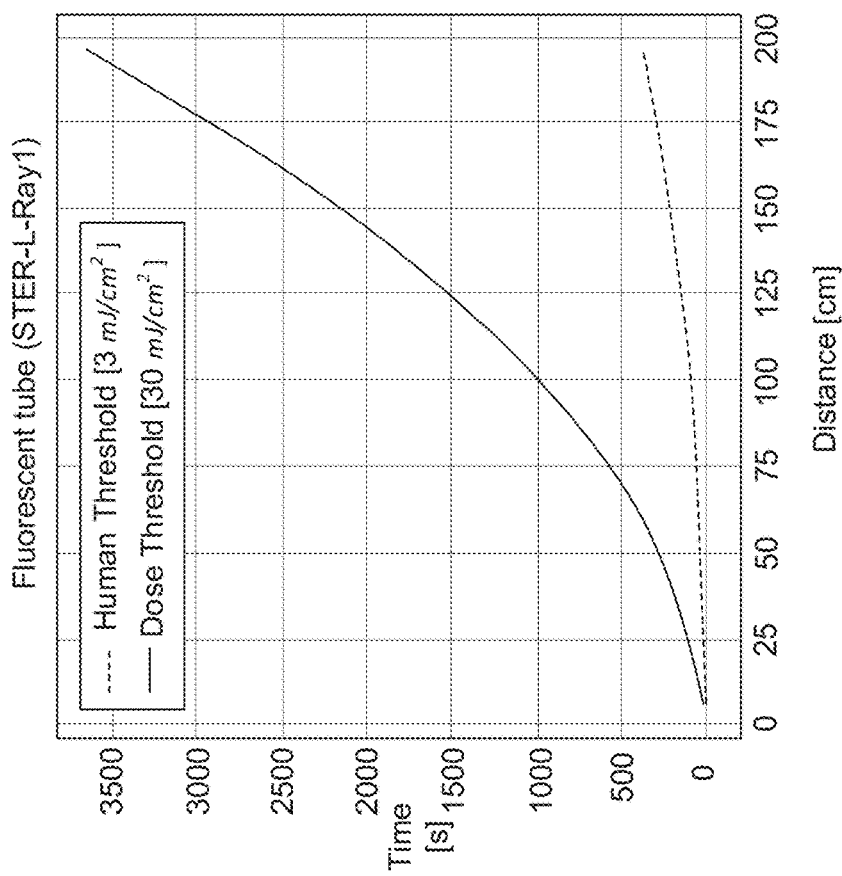

FIG. 11A, FIG. 11B, FIG. 12A, and FIG. 12B illustrate plots 1100, 1150, 1200, and 1250 generated in accordance with one or more embodiments. By way of example, FIG. 11A and FIG. 11B plot the time required for a human to reach an exposure threshold of 3 mJ/cm$^2$ and for a microbe to reach a dose threshold of 30 mJ/cm$^2$ at various distances from the source, as computed with the field intensity model using different fluorescent tubes. In FIG. 11A, with a small fluorescent tube, a human could spend 1.5 minutes within 1 meter of the source within an 8 hour workday without exceeding the daily exposure limit outlined in EU Directive 2006/25/EC. In FIG. 11B, with a large fluorescent tube, it would be safe to spend 1 second within 1 meter of the source. FIGS. 12A and 12B plot the dose received over time at various distances from the source for small and large fluorescent tubes.

Figure 13:
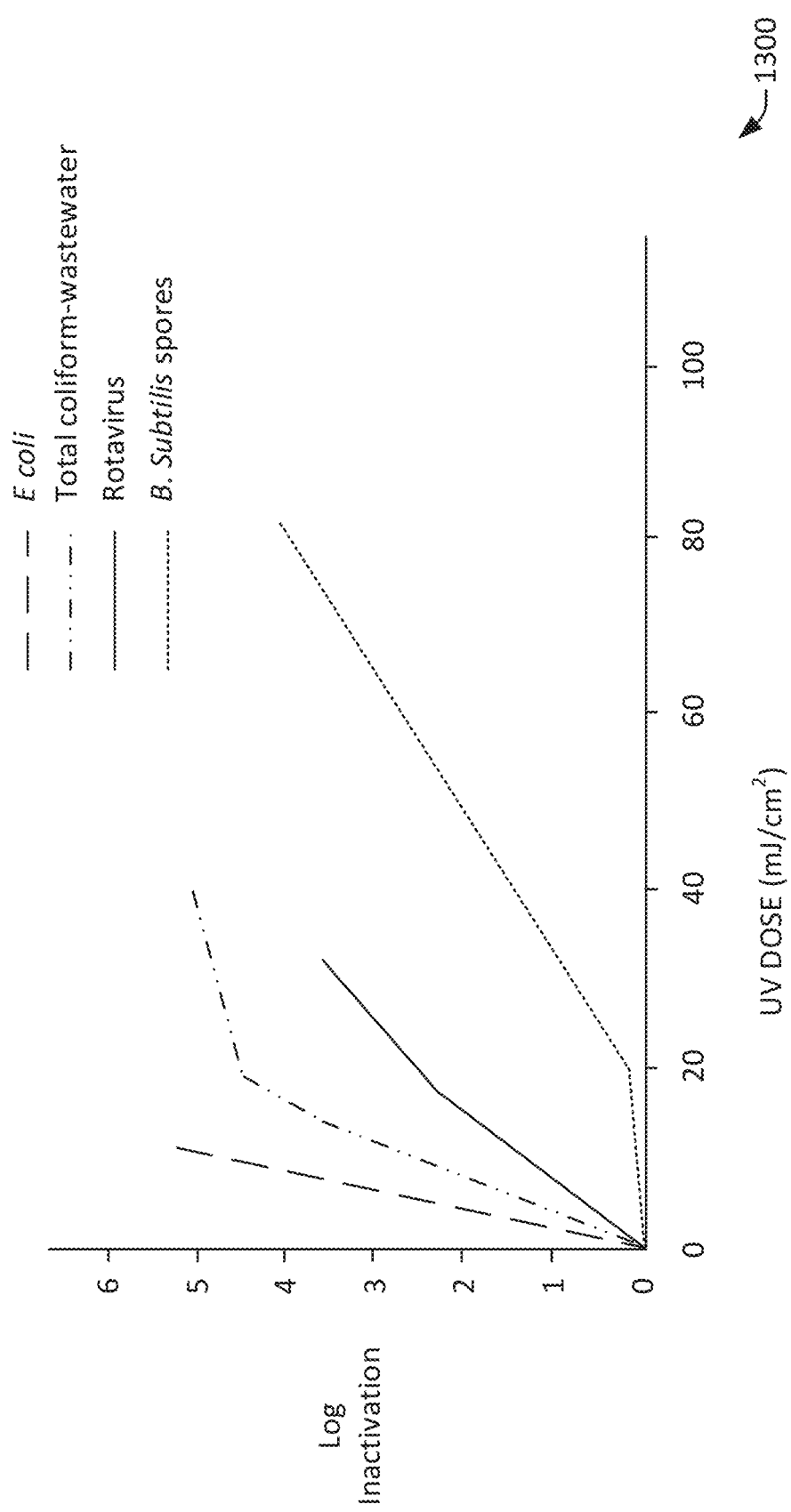
FIG. 13 illustrates a plot generated in accordance with one or more embodiments.

FIG. 13 illustrates a plot 1300 generated in accordance with one or more embodiments. FIG. 13 plots the dose-response curves for various pathogens, with log inactivation on the Y-axis and the UV dose on the X-axis. As shown in FIG. 13, different pathogens exhibit different dose-response curves, including dose-response curves that are non-linear.

FIG. 14A, FIG. 14B, FIG. 15A, FIG. 15B, FIG. 15C, FIG. 16, FIG. 17, FIG. 18, FIG. 19, FIG. 20, and FIG. 21 illustrate cleaning robots, configured in accordance with one or more embodiments. Each of the cleaning robots includes a robotic arm coupled with a chassis and having attached thereto a UV light source.

Figure 15C:
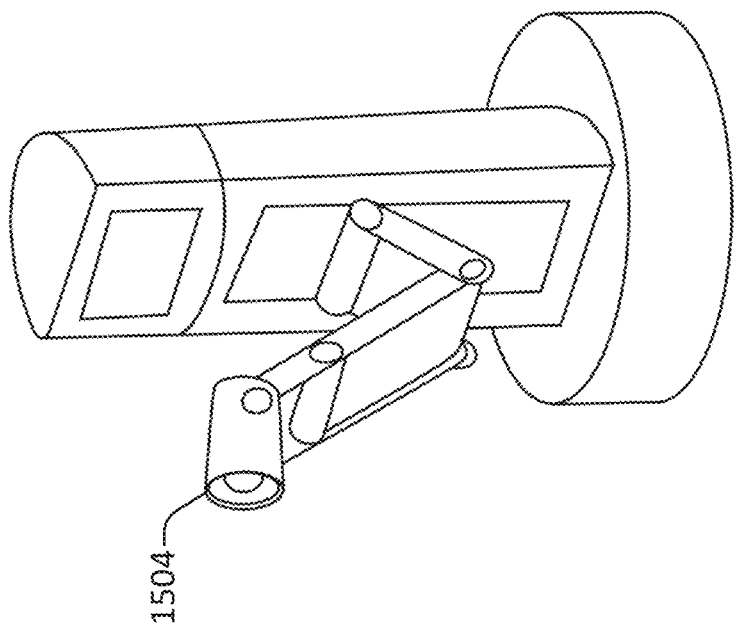
Figures 15A, 15B:
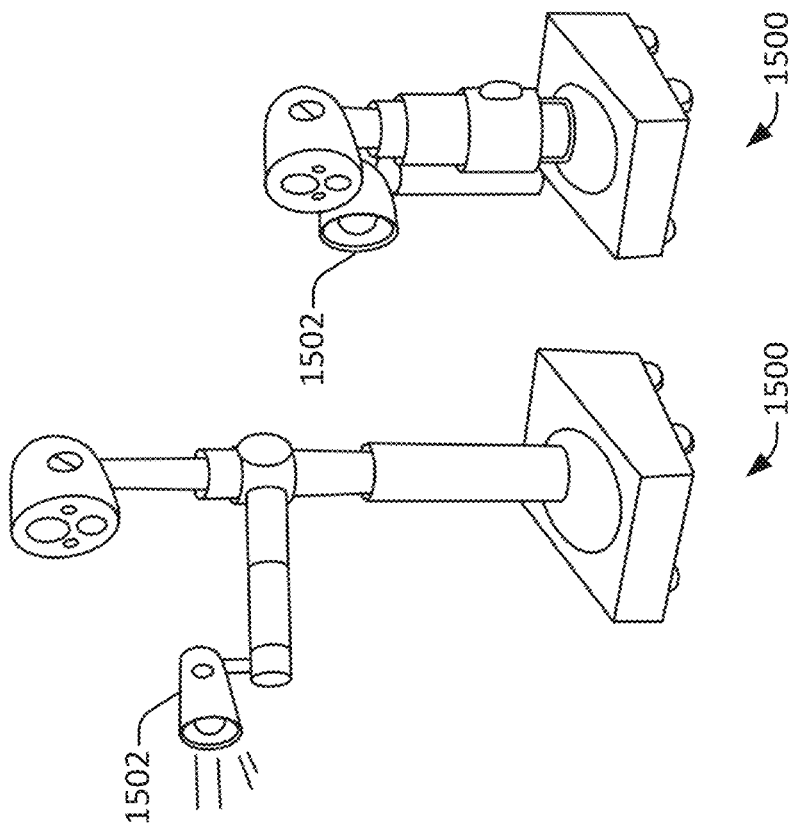

In FIG. 14A, a cleaning robot 1400 is shown with a multi-jointed arm 1402 providing multiple degrees of freedom of movement. In FIG. 14B, a cleaning robot 1450 is shown with an arm 1404 having fewer joints, providing for a simpler construction but fewer degrees of freedom of movement. In FIG. 15A, a compact cleaning robot 1500 is shown with an arm 1502 that extends from the robot. In FIG. 15B, the same robot 1500 is shown in a collapsed state, with the arm 1502 retracted. In FIG. 15C, a cleaning robot 1550 is shown with an arm 1504 that extends directly in front of the robot and that can raise and lower.

Figure 16:
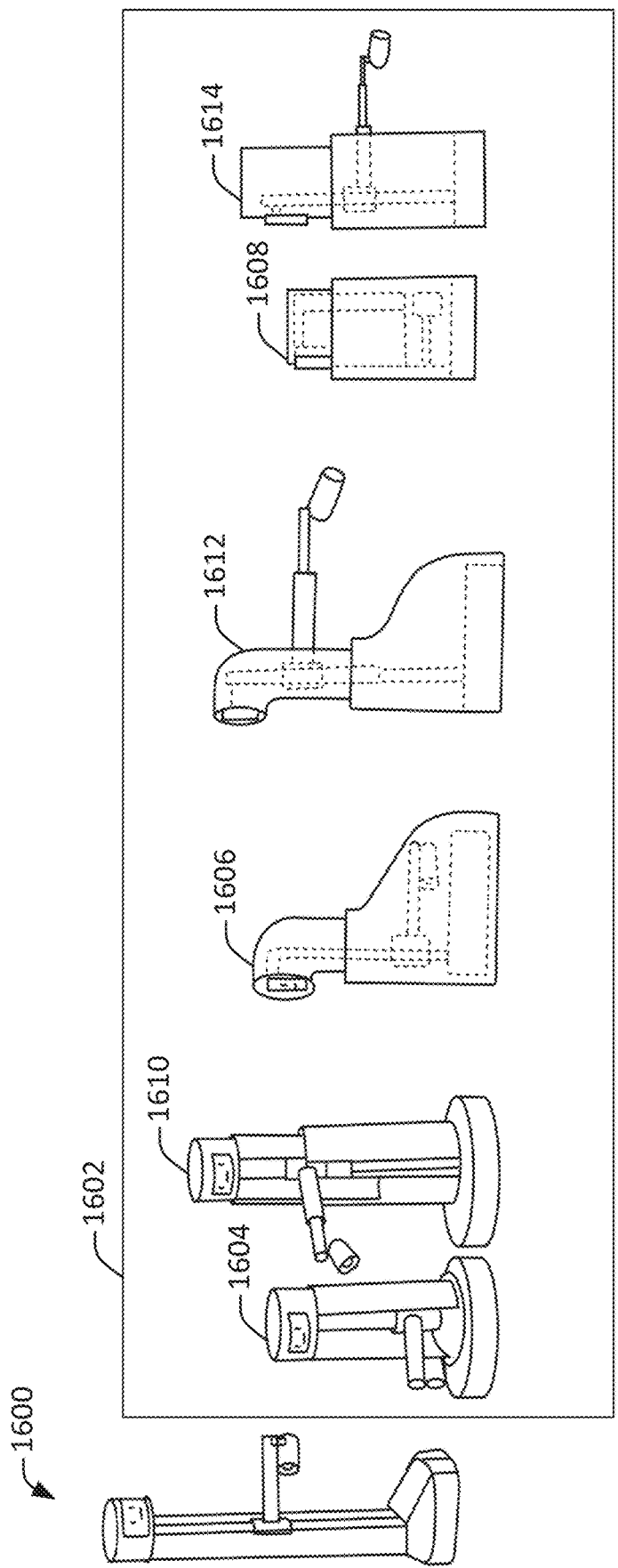

In FIG. 16, a cleaning robot 1600 is shown in configuration with 360-degree panning of a face represented on a display screen, along with a height extension ability. Different perspective views of robots having similar configurations are shown at 1602. At 1604, 1606, and 1608, robots are shown in a collapsed state with height reduced and arm folded. Similarly, in 1610, 1612, and 1614, the same robots are shown in an expanded state.

Figure 17:
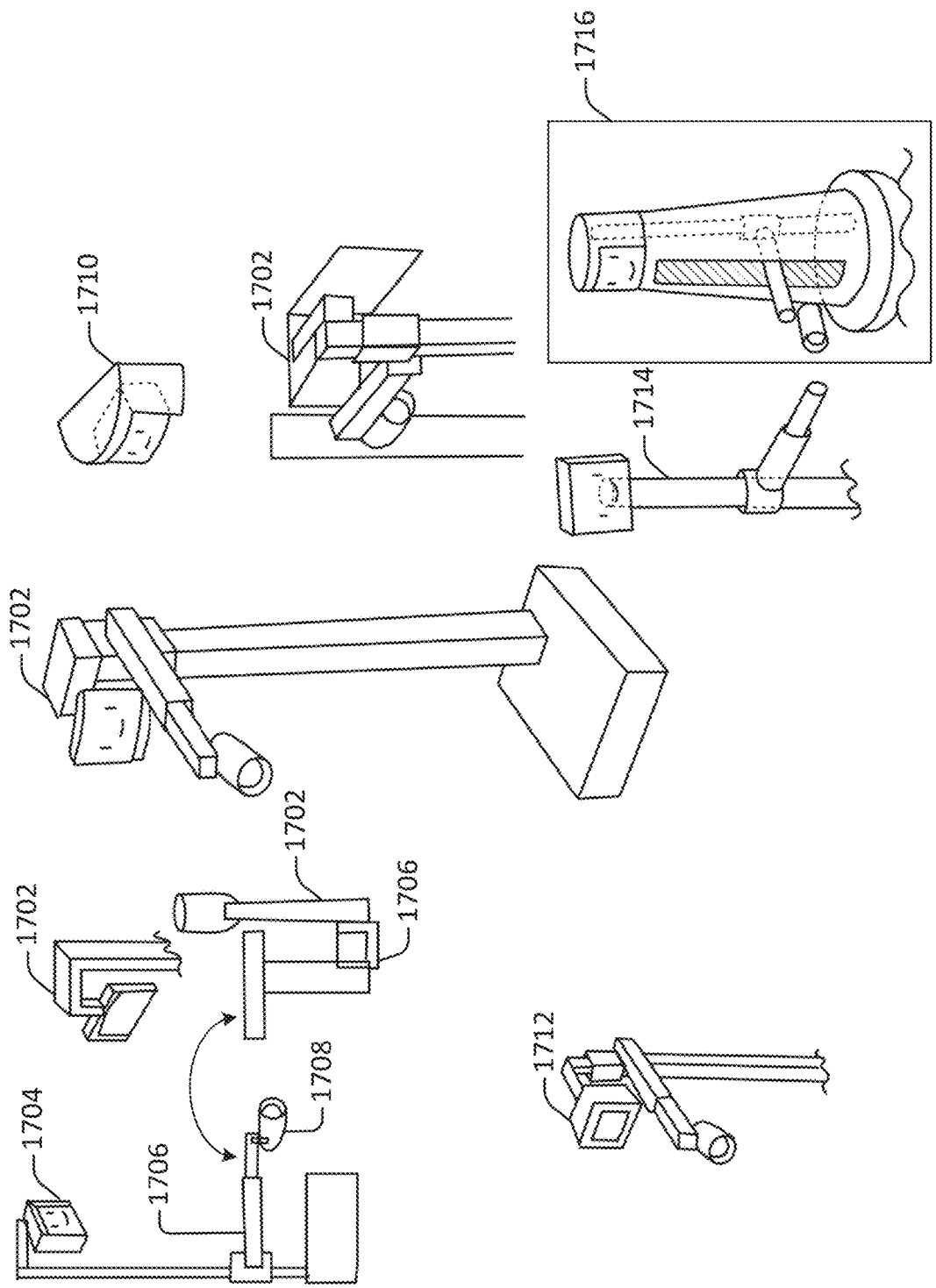

In FIG. 17, various configurations of cleaning robots are shown. At 1702, a cleaning robot is configured with a display screen 1704 that serves as a virtual face. The cleaning robot 1702 is equipped with an arm 1706 having a UV light source 1708. The arm 1706 may be extended or retracted. At 1710 and 1712, alternatives configuration for the display screen are shown. At 1714 and 1716, alternative configurations for the cleaning robot are shown. At 1716, a robotic arm with a UV light source is configured to retract within a cavity of the cleaning robot 1716.

Figure 18:
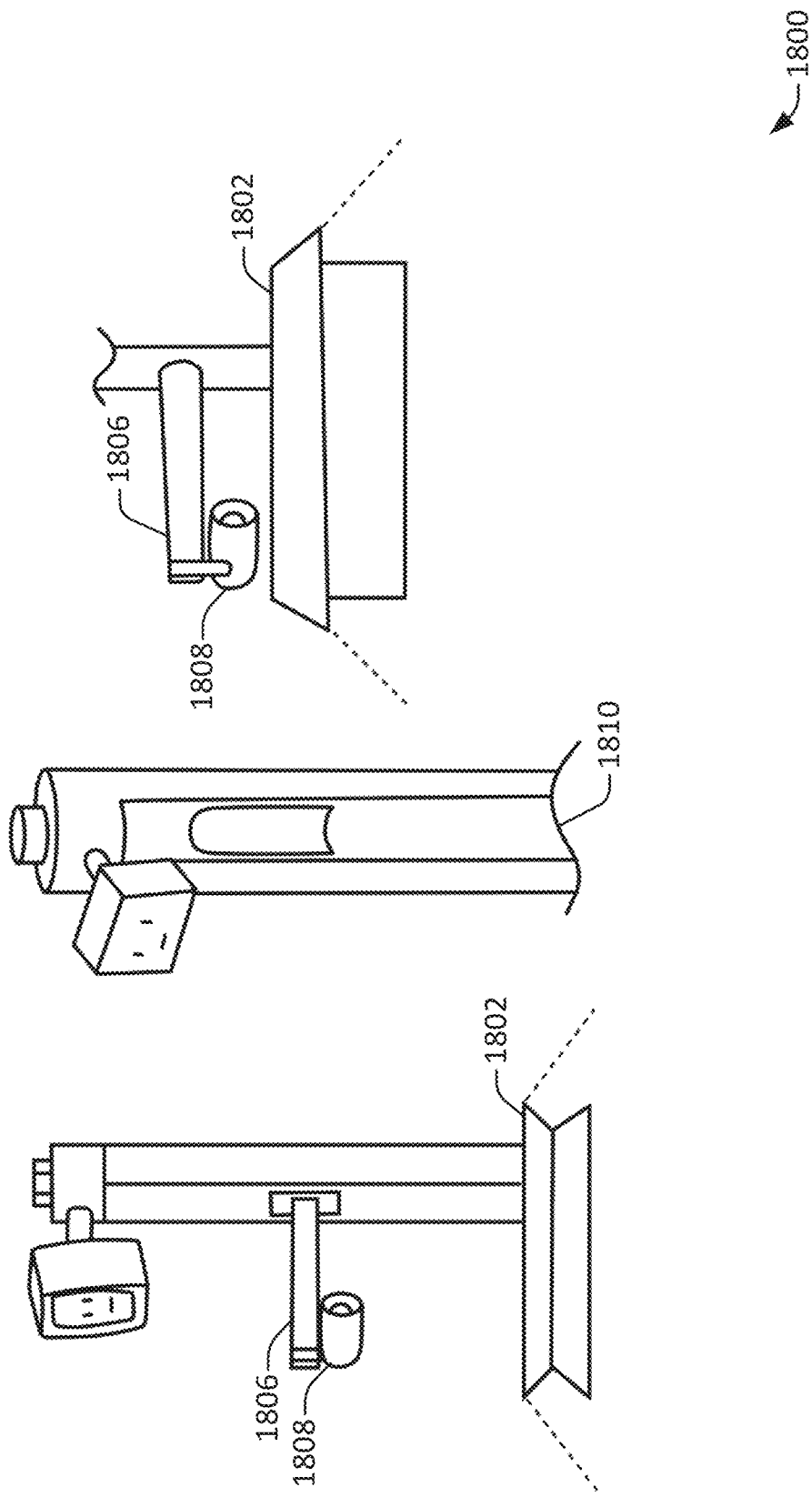

In FIG. 18, a cleaning robot 1800 is shown in various configuration. The arm 1806 includes a movable UV light source 1808. Angled LED lights 1802 on the bottom may help to illuminate a safety boundary area around the robot. The cleaning robot 1800 is configured with a cavity 1810 into which the light source 1808 and arm 1806 may retract.

Figure 19:
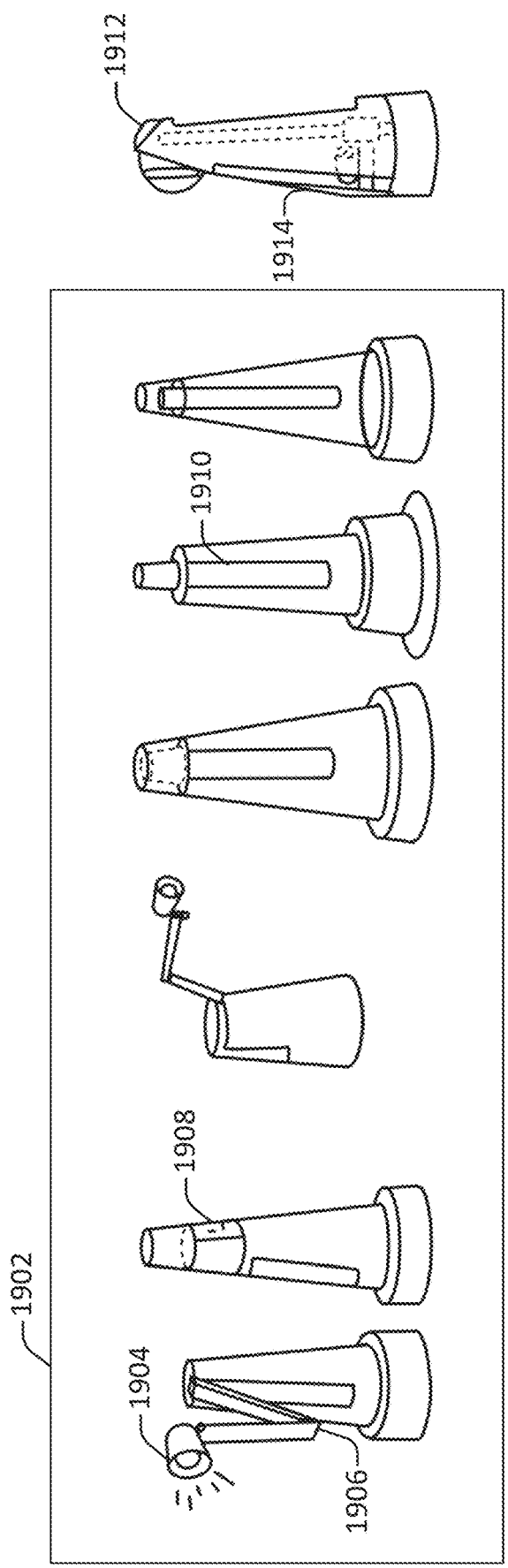

In FIG. 19, a cleaning robot is shown in various configurations 1902 with a cleaning light 1904 that is integrated as part of the body when not in use. For example, the cleaning light 1904 may be configured on an arm 1906 such that the light may be positioned at the top of the robot, like a hat, when not in use. Such configurations may include a display screen 1908, which may operate as a face. The arm may be configured to extend from the robot chassis as shown at 1906, or alternatively may extend directly from the top of the robot chassis as shown at 1910. An alternative configuration is shown at 1912, with the robotic arm extending from the front of the robot at 1914.

Figure 20:
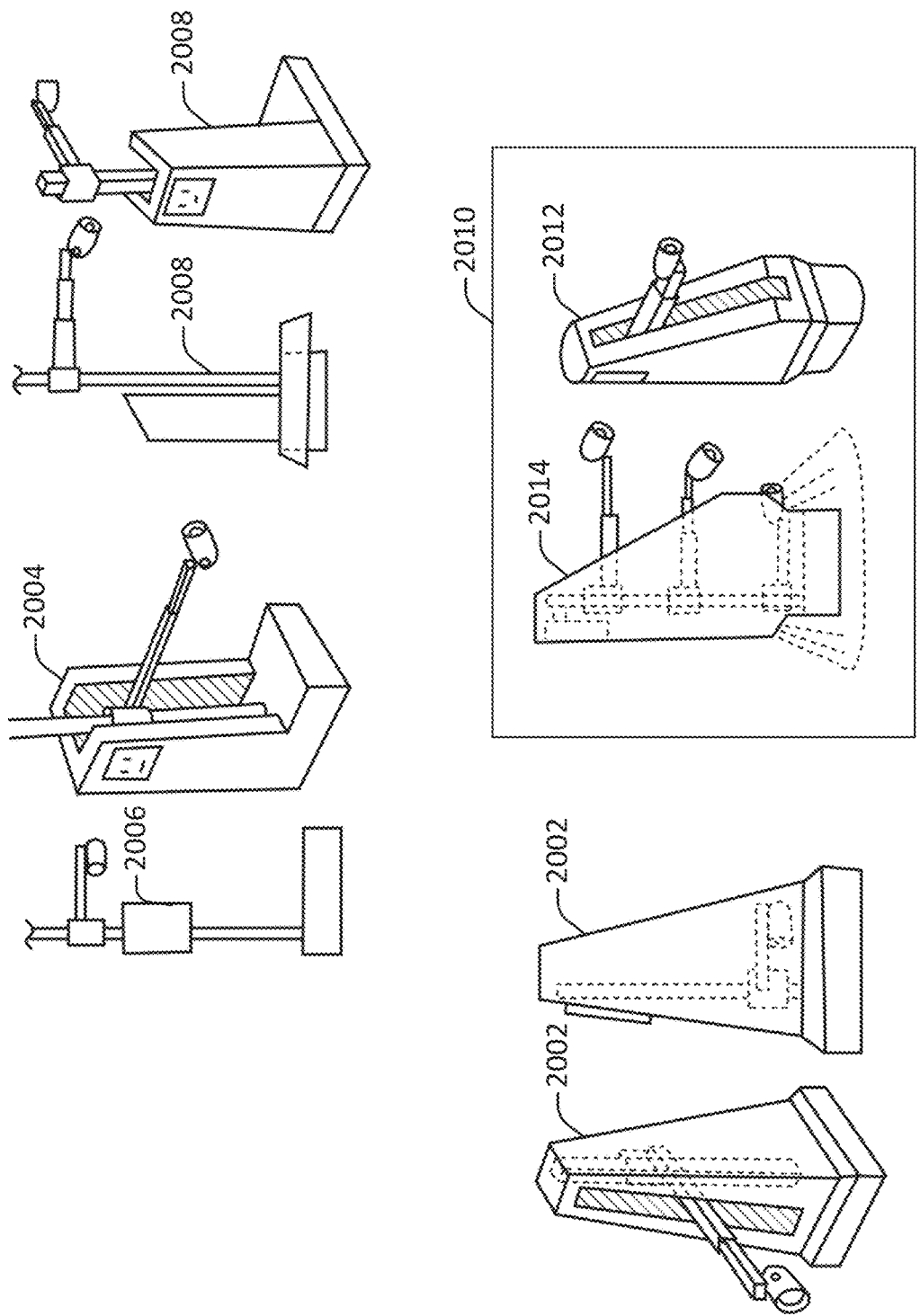

In FIG. 20, a cleaning robot is shown in various configurations in which a robotic arm and attached UV light source retract into the robot when not in use. At 2002, the cleaning robot includes an arm and light source that retract into an interior cavity. At 2006, a box-shaped cavity may be arranged on a central pole, into which the arm may retract. At 2004 and 2008, the cavity of a different shape is shown, with a display screen on the side of the robot. In some configurations, the robotic arm may be mounted on a pole, which itself may move on a base that is attached to a chassis.

At 2010, a configuration is shown in which a robotic arm having a UV light source may retract into a cavity within the robot chassis. As shown at 2012, the robotic arm and light source may both be movable. Further, one or more light sources may be projected downward onto the floor at 2014, for instance to identify a region into which humans should not enter.

Figure 21:
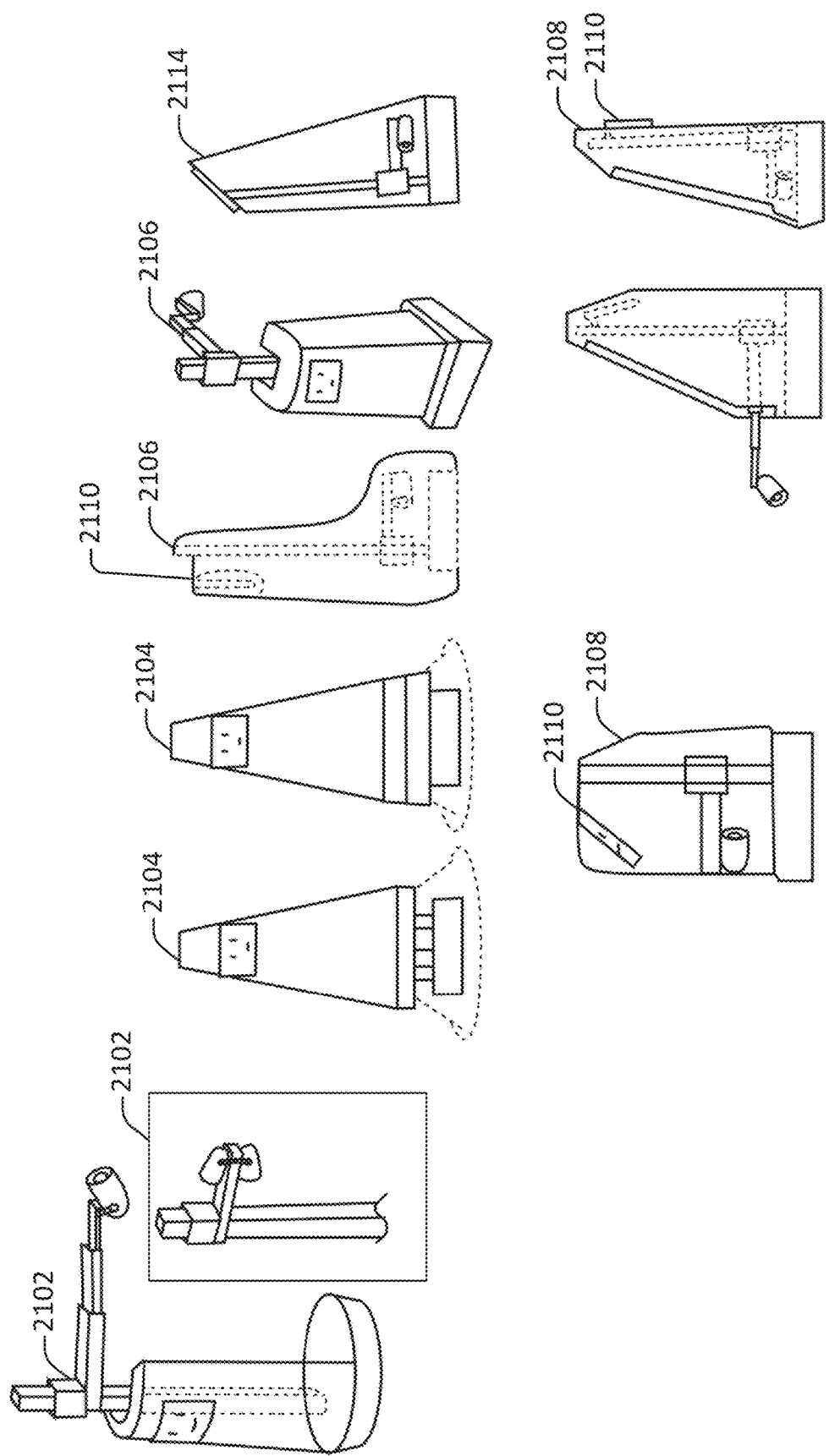

In FIG. 21, a cleaning robot is shown in a variety of configurations. For example, at 2102, the cleaning robot is equipped with a UV light source at the end of a retractable arm, on which the UV light source can swing in a vertical direction. At 2104, the cleaning robot is equipped with a light that projects downward onto the floor, for instance to communicate with humans. At 2106, the cleaning robot is shown equipped with a robotic arm and UV light source that extends out from the back of the chassis. At 2108 and 2106, the cleaning robot is shown configurations in which the display screen 2110 may also be retracted into the chassis. At 2114, the robotic arm is retracted into the chassis.

In the foregoing specification, various techniques and mechanisms may have been described in singular form for clarity. However, it should be noted that some embodiments include multiple iterations of a technique or multiple instantiations of a mechanism unless otherwise noted. For example, a system uses a processor in a variety of contexts but can use multiple processors while remaining within the scope of the present disclosure unless otherwise noted.

Similarly, various techniques and mechanisms may have been described as including a connection between two entities. However, a connection does not necessarily mean a direct, unimpeded connection, as a variety of other entities (e.g., bridges, controllers, gateways, etc.) may reside between the two entities.

In the foregoing specification, reference was made in detail to specific embodiments including one or more of the best modes contemplated by the inventors. While various implementations have been described herein, it should be understood that they have been presented by way of example only, and not limitation. For example, some techniques and mechanisms are described herein in the context of cleaning via UV light. However, the techniques of the present invention apply to a wide variety of cleaning techniques. Particular embodiments may be implemented without some or all of the specific details described herein. In other instances, well known process operations have not been described in detail in order not to unnecessarily obscure the present invention. Accordingly, the breadth and scope of the present application should not be limited by any of the implementations described herein, but should be defined only in accordance with the claims and their equivalents.

The invention claimed is:

1. A robot comprising:
a sensor module operable to collect sensor data characterizing a physical environment around the robot;
a processor operable to determine a three-dimensional model of the physical environment based at least in part on the sensor data and to identifying a designated surface to clean within the physical environment based at least in part on the three-dimensional model;
a mobility apparatus operable to navigate the physical environment, wherein the processor is operable to cause the robot to autonomously navigate to a designated location proximate to the designated surface via the mobility apparatus;
an ultraviolet light source operable to emit electromagnetic radiation in a range capable of cleaning the designated surface, wherein the processor is further operable to clean the designated surface by autonomously activating the ultraviolet light source for a designated period of time; and
a robotic arm capable of movement with respect to the robot in one or more dimensions, the ultraviolet light source being coupled with the robotic arm, wherein the processor is further operable to autonomously move the robotic arm to bring the ultraviolet light source in proximity with the designated surface, wherein the processor is further operable to determine a path through space for the robotic arm that will expose the designated surface to a level of electromagnetic radiation that exceeds a designated threshold, and wherein autonomously moving the robotic arm involves moving the robotic arm along the path through space, wherein the processor is further operable to identify a presence and a corresponding location of a human being within the physical environment, wherein the processor is further operable to calculate a predicted UV exposure dosage estimate for the human from activating the ultraviolet light source, and wherein the processor is further operable to activate the ultraviolet light source only when the predicted UV exposure dosage estimate does not exceed a designated threshold.

2. The robot recited in claim 1, wherein the ultraviolet light source is capable of orientation with respect to the robotic arm in one or more dimensions.

3. The robot recited in claim 1, wherein autonomously navigating to the designated location involves avoiding the corresponding location.

4. The robot recited in claim 1, further comprising a user interface operable facilitating communication between the robot and a human located proximate to the robot in the physical environment.

5. The robot recited in claim 1, wherein the robot is operable to:
autonomously determine that a human is moving along a path that is predicted to approach the robot;
autonomously deactivate the ultraviolet light source; and
autonomously navigate away from the predicted path.

6. The robot recited in claim 5, wherein the robot is operable to:
autonomously determine that the human has moved away from the designated surface; and
autonomously resume cleaning the designated surface.

7. The robot recited in claim 1, wherein the robot is operable to:
autonomously detect a human approaching the robot while the ultraviolet light source is emitting electromagnetic radiation;
deactivate the ultraviolet light source; and
provide a warning indication to the human.

8. The robot recited in claim 1, wherein the designated surface is one of a plurality of surfaces within the physical environment, and wherein the processor is further configured to identify a subset of the surfaces for cleaning, to autonomously determine a plan for cleaning each of the subset of the surfaces, and to autonomously operate the mobility apparatus and the ultraviolet light source to implement the plan.

9. The robot recited in claim 1, wherein the sensor module includes a camera, and wherein the sensor data includes image data collected from the physical environment.

10. The robot recited in claim 1, wherein the sensor module includes a depth sensor, and wherein the sensor data includes depth information indicating a plurality of distances from the depth sensor to a plurality of objects within the physical environment.

11. The robot recited in claim 1, a communication interface operable to receive an instruction from a remote communication device, the instruction designating a portion of the physical environment for cleaning.

12. A method comprising:
collecting sensor data characterizing a physical environment around a robot via a sensor module;
determining via a processor a three-dimensional model of the physical environment based at least in part on the sensor data;
identifying via the processor a designated surface to clean within the physical environment based at least in part on the three-dimensional model;
autonomously navigating the robot through the physical environment to a designated location proximate to the designated surface via a mobility apparatus;
identifying a presence and a corresponding location of a human being within the physical environment;
determining a path through space for a robotic arm coupled with the robot that will expose the designated surface to a level of electromagnetic radiation that exceeds a designated threshold, the robotic arm capable of movement with respect to the robot in one or more dimensions;
calculating a predicted UV exposure dosage estimate for the human from activating the ultraviolet light source;

autonomously moving a robotic along the path through space to bring the ultraviolet light source in proximity with the designated surface; and autonomously activating an ultraviolet light source coupled with the robotic arm for a designated period of time, the ultraviolet light source emitting electromagnetic radiation in a range capable of cleaning the designated surface, wherein the processor is further operable to activate the ultraviolet light source only when the predicted UV exposure dosage estimate does not exceed a designated threshold.

13. The method recited in claim 12, further comprising:

autonomously determining that a human is moving along a path that is predicted to approach the robot;

autonomously deactivating the ultraviolet light source;

autonomously navigating away from the predicted path;

autonomously determining that the human has moved away from the designated surface; and autonomously resuming cleaning of the designated surface.

* * * * *